United States Patent
Ross

(10) Patent No.: US 6,255,055 B1
(45) Date of Patent: Jul. 3, 2001

(54) C-MYC CODING REGION DETERMINANT-BINDING PROTEIN (CRD-BP) AND ITS NUCLEIC ACID SEQUENCE

(75) Inventor: Jeffrey Ross, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/261,855

(22) Filed: Mar. 3, 1999

Related U.S. Application Data

(60) Provisional application No. 60/077,372, filed on Mar. 9, 1998.

(51) Int. Cl.[7] .................. G01N 33/53; G01N 33/574; G01N 33/48; C12P 19/34
(52) U.S. Cl. ................. 435/7.1; 435/7.3; 435/91.2; 436/64
(58) Field of Search .................... 435/7.23, 7.1, 435/91.2; 436/64

(56) References Cited

PUBLICATIONS

"Control of c–myc MRNA half–life in vitro by a protein capable of binding to a coding regional stability determinant," P.L. Bernstein, D.J. Herrick, R.D. Prokipcak and J. Ross, *Genes & Development*, 6:652–654 (1992).

"The Half–Life of c–myc mRNA in Growing and Serum–Stimulated Cells: Influence of the Coding and 3' Untranslated Regions and Role of Ribosome Translocation," D.J. Herrick and J. Ross, *Mol. Cell. Biol.*, 14:2119–2128 (Mar., 1994).

"Purification and Properties of a Protein That Binds to the C–terminal Coding Region of Human c–myc mRNA," R.D. Prokipcak, D.J. Herrick and J. Ross, *J. Biol. Chem.*, 269:9261–9269 (Mar. 25, 1994).

"MRNA Stability in Mammalian Cells," J. Ross, *Microbiol. Rev.*, 59:423–450 (Sep., 1995).

"Developmental regulation of CRD–BP, an RNA–binding protein that stabilizes c–myc mRNA in vitro," P.Leeds, B.T. Kren, J.M. Boylan, N.A. Betz, C.J. Steer, P.A. Gruppuso and J. Ross, *Oncogene*, 14:1279–1286 (1997).

"The c–myc coding region determinant–binding protein: a member of a family of KH domain RNA–binding proteins," G.A.R. Doyle, N.A. Betz, P.F. Leeds, A.J. Fleisig, R.D. Prokipcak and J. Ross, *Nucleic Acids Research*, 26:5036–5044 (1998).

G.A.R. Doyle, et al., "The c–myc coding region determinant–binding protein: a member of a family of KH domain RNA–binding proteins," *Nucleic Acids Research*, 26:503–5044 (1998).

P. Leeds, et al., "Developmental regulation of CRD–BP, an RNA–binding protein that stabilizes c–myc mRNA in vitro," *Oncogene*, 14:1279–1286 (1997).

F. Müeller–Pillasch et al., "Cloning of a gene highly overexpressed in Cancer coding for a novel KH–domain containing protein," *Oncogene*, 14:2729–2733 (1997).

*Primary Examiner*—Anthony C. Caputa
*Assistant Examiner*—Jennifer Hunt
(74) *Attorney, Agent, or Firm*—Quarles & Brady LLP

(57) ABSTRACT

A method of diagnosing the presence or absence of cancer in a human patient is disclosed. In one embodiment, this method comprises the steps of examining patient tissue for the CRD-BP expression levels and comparing that expression level with control levels. The present invention is also a method of inhibiting cancer cell growth comprising the step of eliminating or lowering the level of functional CRD-BP in the cancerous tissues.

1 Claim, 13 Drawing Sheets

FIG.1A

```
  1  GGGTGGGTGGTAGAAAGTTTGCGGCTCCCGCCCGTATCCACGCCTATCGGCATAG
 61  GAGGATATCCGCCCGCCCCGCCCCGGATCGGCATTGAACAGTGTCCTTGCCCGC
121  CACCGCCACCATGAACAAGCTTTACATCGGCAACCTCAACGAGAGTGTGACCCCGCAGA
  1                M  N  K  L  Y  I  G  N  L  N  E  S  V  T  P  A  D

181  CTTGGAGAAAGTATTCGCGGAGCACAAGATCTCCTACAGCGGCCAGTTCTTGGTCAAATC
 18   L  E  K  V  F  A  E  H  H  K  I  S  Y  S  G  Q  F  L  V  K  S

241  CGGCTACGCCTTCGTGGATTGCCCCGACGAGCACTGGGCCATGAAGGCCATCGAAACTTT
 38    G  Y  A  F  V  D  C  P  D  E  H  W  A  M  K  A  I  E  T  F

301  CTCGGGGAAAGTAGAACTGCAAGGAAAACGTCTAGAGATTGAACACTCAGTCCCCAAAAA
 58   S  G  K  V  E  L  Q  G  K  R  L  E  I  E  H  S  V  P  K  K

361  ACAAAGGAGTCGGAAAATACAGATCCGCAATATTCCACCTCAGCTCCGATGGGAAGTGCT
 78    Q  R  S  R  K  I  Q  I  R  N  I  P  P  Q  L  R  W  E  V  L

421  AGATAGCCTGCTGGCTCAGTACGGTCACCTACTCTAACGTGAGCAAGTGAACACTGAAAG
 98    D  S  L  L  A  Q  Y  G  T  V  E  N  C  E  Q  V  N  T  E  S

481  TGAGACAGCGGTGGTCAACGTCACCTACTCTAACCGGGAGCAGACCAGGCAAGCTATCAT
118    E  T  A  V  V  N  V  T  Y  S  N  R  E  Q  T  R  Q  A  I  M

541  GAAGCTAAATGGCCATCAACTGGAGAACCATGCCCTGAAGGTCTCCTACATACCTGATGA
138    K  L  N  G  H  Q  L  E  N  H  A  L  K  V  S  Y  I  P  D  E
```

FIG. 1B

```
601  GCAGATAACACAAGGTCCTGAGAATGGGCGTCGTGGAGGCTTTGGGTCTCGGGGCCAGCC
158   Q  I  T  Q  G  P  E  N |R  R  G  G  F  G  S  R  G  Q  P|
661  CCGGCAAGGGTCGCCCGTGGCAGCAGGGCTCCAGCAAGCAGCCAGTGACATCCC
178  |R  Q  G| S  P  V  A  A  G  A  P  A  K  Q  Q  P  V  D  I  P
721  TCTCCGGCTCCCCTGGTGCCTACGCAGTATGTAGGCGCTATCATTGGCAAGGAGGGTGCCAC
198   L  R  L  L  V  P  T  Q  Y  V  G  A  I  I  G  K  E  G  A  T
781  CATCCGAAACATCACAAAACAGACGCAGTCCAAAATAGACGTGCATAGGAAGGAGAATGC
218   I  R  N  I  T  K  Q  T  Q  S  K  I  D  V  H  R  K  E  N  A
841  GGGCGCTGCGGAGAAGGCCATCAGCGTGCATTCAACCCCTGAAGGCTGCTCCTCCGCGTG
238   G  A  E  K  A  I  S  V  H  S  T  P  E  G  C  S  S  A  C
901  CAAGATGATCTTGGAGATTATGCACAAGGAGGCAAAGGACACCAAAACGGCAGATGAAGT
258   K  M  I  L  E  I  M  H  K  E  A  K  D  T  K  T  A  D  E  V
961  TCCCCTGAAGATCCTGGCTCATAACAACTTCGTCGGGCGACTCATTGGCAAGGAAGGCCG
278   P  L  K  I  L  A  H  N  N  F  V  G  R  L  I  G  K  E  G  R
1021 GAACCTGAAGAAGGTGGAGCAGGACACAGAGACGAAGATCACCATCTCATCGCTCCAGGA
298   N  L  K  K  V  E  Q  D  T  E  T  K  I  T  I  S  S  L  Q  D
```

FIG. IC

```
1081 CCTCACGCTCTATAACCCTGAGAGGACCATCACTGTGAAGGGGCCATTGAGAACTGTTG
 318       L   T   L   Y   N   P   E   R   T   I   T   V   K   G   A   I   E   N   C   C

1141 CAGGGCCGAGCAGGAGATCATGAAGAAAGTTCGAGAGGCTTACGAGAACGACGTGGCCGC
 338       R   A   E   Q   E   I   M   K   K   V   R   E   A   Y   E   N   D   V   A   A

1201 CATGAGCTTGCAGTCCCACCTCATCCCTGGGCTTAACCTGGCTGCTGTAGGTCTCTTCCC
 358       M   S   L   Q   S   H   L   I   P   G   L   N   L   A   A   V   G   L   F   P

1261 AGCTTCATCCAGCCTGTCCCCTCCTCCCAGCAGTGTCACTGGGGCTGCTCCCTATAG
 378       A   S   S   A   V   P   P   P   S   S   V   T   G   A   A   P   Y   S

1321 CTCCTTCATGCAGGCTCCGAGCAGGAGATGGTTCAAGTGTTCATCCCGCCCAGCTGT
 398       S   F   M   Q   A   P   E   Q   E   M   V   Q   V   F   I   P   A   Q   A   V

1381 GGGCGGCCATCATTGGCAAGAAGGGCCAGCACATCAAACTCTCCCGTTTCGCCAGCGC
 418       G   A   I   I   G   K   K   G   Q   H   I   K   Q   L   S   R   F   A   S   A

1441 CTCCATCAAGATTGCTCCACCAGAAACACCTGACTCCAAAGTTCGAATGGTCGTCATCAC
 438       S   I   K   I   A   P   P   E   T   P   D   S   K   V   R   M   V   V   I   T

1501 TGGACCCCCAGAGGCTCAGTTCAAGGCTCAGGGAAGAATTTATGGCAAACTAAAAGAAGA
 458       G   P   P   E   A   Q   F   K   A   Q   G   R   I   Y   G   K   L   K   E   E
```

FIG. 1D

```
1561 GAATTTCTTTGGTCCCAAGGAGGAAGTAAAGCTAGAGACCCACATACGGGTTCCGGCTTC
 478  N  F  F  G  P  K  E  E  V  K  L  E  T  H  I  R  V  P  A  S
                                              _____

1621 AGCAGCCGGCCGCGTCATCGGCAAAGGCGGCAAGACTGTGAATGAGCTGCAGAACTTGAC
 498  A  A  G  R  V  I  G  K  G  G  K  T  V  N  E  L  Q  N  L  T
      ====================

1681 TGCAGCTGAGGTGGTAGTGCCAAGAGACCAGACCCCGGATGAGAACGACCAAGTCATTGT
 518  A  A  E  V  V  V  P  R  D  Q  T  P  D  E  N  D  Q  V  I  V
      ====================

1741 TAAGATCATCGGACATTTCTATGCCAGCCAGATGGCTCAGCGCTCAGCGAAGATCCGAGACATCCT
 538  K  I  I  G  H  F  Y  A  S  Q  M  A  Q  R  K  I  R  D  I  L
      _____

1801 GGCTCAAGTTAAGCAACAGCACCAGAAGGGACAGAGCAACCTGGCCCAGGCACGGAGGAA
 558  A  Q  V  K  Q  Q  H  Q  K  G  Q  S  N  L  A  Q  A  R  R  K

1861 GTGACCCCCGGCCCCTCCTGTCCCATTGGCTCCAAGATCAGCAGGAGGAACACAGAACTGG
 578  *

1921 AGGGGCGGGTGGAGGCCGGTGTGTTTTCCCAGCAGGCCTGAGAATGAGTGGAATCAG
1981 GGCATTTGGGCCTGGCTGGAGATCAGGTTTGCACACTGTATTGAGAACAATGTTCCAGTG
2041 AGGAATCCTGATCTCTCGCCCCCAATTGAGCCAGCTGGCCACAGCCCACCCCTGGAATA
2101 TCACCATTGCAATCATAGCTTGGGTTGCTTTTAAACGTGGATTGTCTTGAAGTTCTCCAG
2161 CCTCCATGGAAGGATGGTCAGATCCCCAGTGGGGAAGAGAAATAAAATTTCCTTCAGGTT
                                               _____
2221 TTAT
```

FIG. 2A

```
mCRD-BP      R  R  G  G  F  G  S  R  G  Q  P  -  R  Q  G
hKOC         G  R  G  G  L  G  Q  R  G  S  S  -  R  Q  G
hnRNPK       G  R  G  G  F  -  D  R  M  P  P  G  R  G  G
Fibrillarin  G  R  G  G  F  G  G  R  G  G  -  G  R  G  G
Nucleolin    G  R  G  G  F  G  G  R  G  G  -  G  R  G  G
FMRP         L  R  R  G  D  G  R  R  G  G  G  G  G  R  G Consensus:   G  R  G  G  F  G     R  G  G     G  R  G  G
                                  R                    Q
```

FIG. 2B

```
mCRD-BP      Q  L  R  -  -  -  W  E  V  L  D  S  L  L
hKOC         H  L  Q  -  -  -  W  E  V  L  D  S  L  L
FMRP         Q  L  R  -  -  -  L  E  R  L  Q  -  I  D
mCRD-BP      T  I  S  P  L  Q  D  E  L  T  -  -  L  Y
hKOC         T  I  S  P  L  Q  E  L  T  -  -  L  L
REV          Q  L  P  P  L  E  R  L  T  -  -  L  D

Consensus:   Q  L        L  E        L  T        L
             T  I        W  Q        D        I
```

FIG. 2C-1

|   | | | | | | | | | | | |
|---|---|---|---|---|---|---|---|---|---|---|---|
| mCRD-BP(1) | L | L | V | P | T | Q | Y | V | G | A | I | G | K | E | G | A | T | I | R | N | I | T | K |
| mCRD-BP(2) | H | A | A | H | N | N | F | V | G | R | L | I | G | K | E | G | R | N | L | K | K | V | E | Q |
| mCRD-BP(3) | V | F | I | P | A | Q | A | V | G | A | I | I | G | K | K | G | Q | H | I | K | Q | L | S | R |
| mCRD-BP(4) | L | R | V | P | A | S | Q | A | A | G | R | V | I | G | K | G | G | K | T | V | N | E | L | Q |
| hKOC(1) | L | L | A | H | N | N | F | V | G | R | L | I | G | K | E | G | R | N | L | K | K | I | T | K |
| hKOC(2) | Q | F | I | P | T | Q | F | V | G | A | I | V | G | K | K | G | Q | H | I | K | Q | L | S | R |
| hKOC(3) | H | L | L | H | Q | S | L | A | G | G | I | I | G | V | K | G | G | K | N | I | K | E | Q |
| hKOC(4) | I | L | L | P | K | D | L | A | G | S | L | I | G | K | G | G | K | R | I | K | A | L | R | E |
| hnRNPK(1) | F | I | T | P | R | E | D | M | G | L | A | I | G | T | H | G | A | N | I | Q | Q | L | R | H |
| hnRNPK(2) | I | Q | V | P | R | N | L | V | G | K | V | I | G | K | N | G | K | L | I | Q | E | I | A | K |
| hnRNPK(3) | | | | | | | | | | | | | | | | | | | | | | | | |
| FMRP(1) | | | | | | | | | | | | | | | | | | | | | | | | |
| FMRP(2) | | | | | | | | | | | | | | | | | | | | | | | | |
| Consensus: | I | I | | | | | V G | | L I G K G G | | I | | | | I | I |

FIG. 2C-2

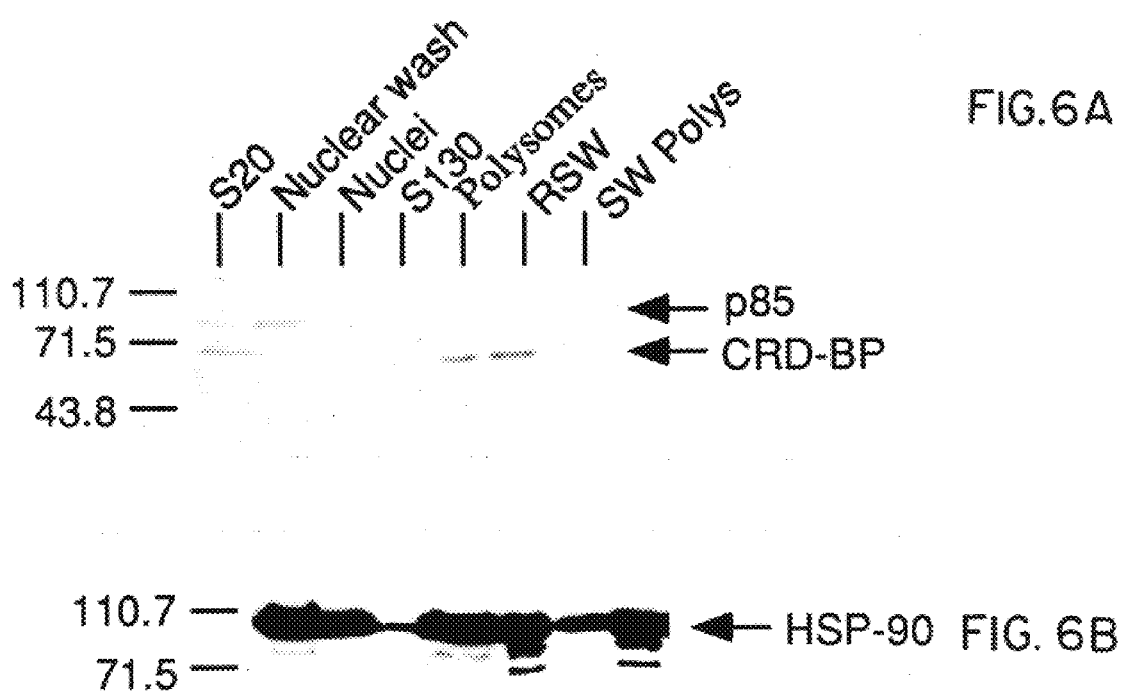

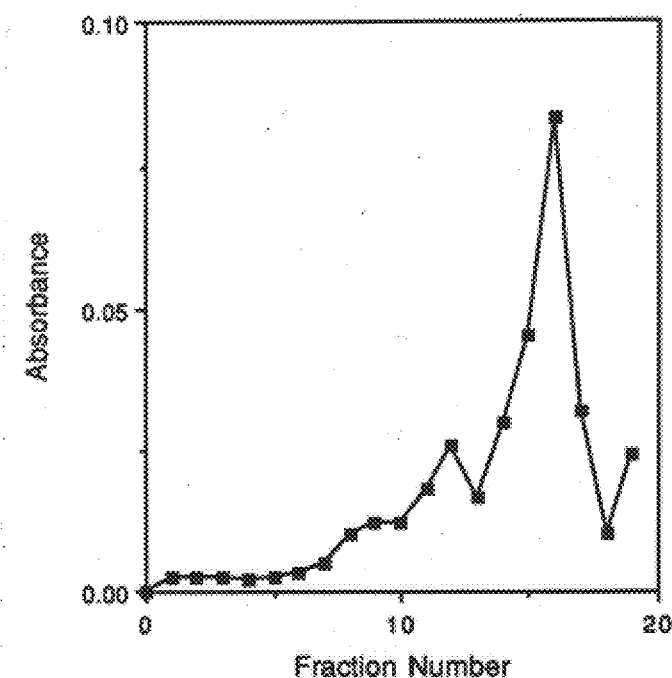
FIG. 7A
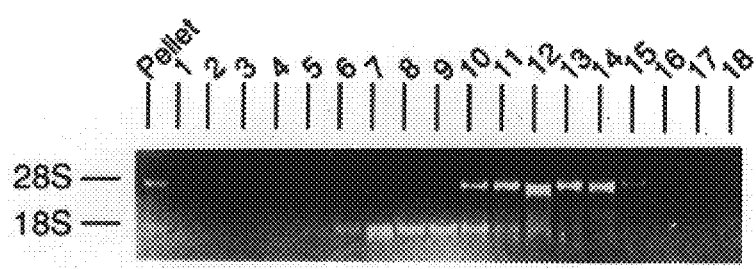
FIG. 7B
FIG. 7C
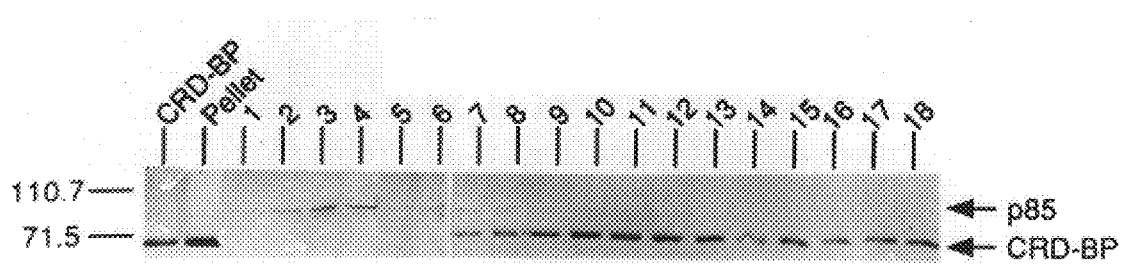

SEQUENCE LISTING

<160> NUMBER OF SEQ ID NOS: 46

<210> SEQ ID NO: 1
<211> LENGTH: 2224
<212> TYPE: DNA
<213> ORGANISM: Mus musculus

<400> SEQUENCE: 1

```
gggtggggtg sgtagaaagt ttgcggctcc cgccgcccgt atccacgcct atcggcatag        60
gaggatatcc gcccgcgccc gcccggatcg gcattgaatg gaacagtgtc cttgccccgc       120
caccgccacc atgaacaagc tttacatcgg caacctcaac gagagtgtga ccccgcagaa       180
cttggagaaa gtattcgcgg agcacaagat ctcctacagc ggccagttct tggtcaaatc       240
cggctacgcc ttcgtggatt gccccgacga gcactgggcg atgaaggcca tcgaaacttt       300
ctcggggaaa gtagaactgc aaggaaaacg tctagagatt gaacactcag tccccaaaaa       360
acaaaggagt cggaaaatac agatccgcaa tattccacct cagctccgat gggaagtgct       420
agatagcctg ctggctcagt acggtacagt ggagaactgt gagcaagtga acactgaaag       480
tgagacagcg gtggtcaacg tcacctactc taaccgggag cagaccaggc aagctatcat       540
gaagctaaat ggccatcaac tggagaacca tgccctgaag gtctcctaca tacctgatga       600
gcagataaca caaggtcctg agaatgggcg tcgtggaggc tttgggtctc ggggccagcc       660
ccggcaaggg tcgcccgtgg cagcaggggc tccagccaag cagcagccag tggacatccc       720
tctccggctc ctggtgccta cgcagtatgt aggcgctatc attggcaagg agggtgccac       780
catccgaaac atcacaaaac agacgcagtc caaaatagac gtgcatagga aggagaatgc       840
gggcgctgcg gagaaggcca tcagcgtgca ttcaaccct gaaggctgct cctccgcgtg       900
caagatgatc ttggagatta tgcacaagga ggcaaaggac accaaaacgg cagatgaagt       960
tcccctgaag atcctggctc ataacaactt cgtcgggcga ctcattggca aggaaggccg      1020
gaacctgaag aagtggagc aggacacaga gacgaagatc accatctcat cgctccagga      1080
cctcacgctc tataaccctg agaggaccat cactgtgaag gcgccattg agaactgttg      1140
cagggccgag caggagatca tgaagaaagt tcgagaggct tacgagaacg acgtggccgc      1200
catgagcttg cagtccccac tcatccctgg gcttaacctg gctgctgtag gtctcttccc      1260
agcttcatcc agcgctgtcc ctcctcctcc cagcagtgtc actggggctg ctccctatag      1320
ctccttcatg caggctccgg agcaggagat ggtacaagtg ttcatcccg cccaggctgt      1380
gggcgccatc attggcaaga agggccagca atcaaacaa ctctcccgtt cgccagcgc      1440
ctccatcaag attgctccac cagaaacacc tgactccaaa gttcgaatgg tcgtcatcac      1500
tggaccccca gaggctcagt tcaaggctca gggaagaatt tatggcaaac taaagaaga      1560
gaatttcttt ggtcccaagg aggaagtaaa gctagagacc cacatacggg ttccggcttc      1620
agcagccggc cgcgtcatcg gcaaaggcgg caaaacggtg aatgagctgc agaacttgac      1680
tgcagctgag gtggtagtgc aagagacca gaccccggat gagaacgacc aagtcattgt      1740
taagatcatc ggacatttct atgccagcca gatggctcag cggaagatcc gagacatcct      1800
ggctcaagtt aagcaacagc accagaaggg acagagcaac ctggcccagg cacggaggaa      1860
gtgaccccgc ccctcctgt cccattggct ccaagatcag caggaggaac acagaactgg      1920
aggggcgggt ggagggccgg tgtgtttttc ccagcaggcc tgagaatgag tgggaatcag      1980
ggcatttggg cctggctgga gatcaggttt gcacactgta ttgagaacaa tgttccagtg      2040
aggaatcctg atctctcgcc cccaattgag ccagctggcc acagcccacc ccttggaata      2100
tcaccattgc aatcatagct tgggttgctt ttaaacgtgg attgtcttga agttctccag      2160
cctccatgga aggatgggtc agatcccagt ggggaagaga aataaaattt ccttcaggtt      2220
ttat                                                                   2224
```

```
<210> SEQ ID NO: 2
<211> LENGTH: 577
<212> TYPE: PRT
<213> ORGANISM: Mus musculus

<400> SEQUENCE: 2

Met Asn Lys Leu Tyr Ile Gly Asn Leu Asn Glu Ser Val Thr Pro Ala
 1               5                  10                  15

Asp Leu Glu Lys Val Phe Ala Glu His Lys Ile Ser Tyr Ser Gly Gln
            20                  25                  30

Phe Leu Val Lys Ser Gly Tyr Ala Phe Val Asp Cys Pro Asp Glu His
        35                  40                  45

Trp Ala Met Lys Ala Ile Glu Thr Phe Ser Gly Lys Val Glu Leu Gln
    50                  55                  60

Gly Lys Arg Leu Glu Met Glu His Ser Val Pro Lys Lys Gln Arg Ser
65                  70                  75                  80

Arg Lys Ile Gln Ile Arg Asn Ile Pro Pro Gln Leu Arg Trp Glu Val
                85                  90                  95

Leu Asp Ser Leu Leu Ala Gln Tyr Gly Thr Val Glu Asn Cys Glu Gln
            100                 105                 110

Val Asn Thr Glu Ser Glu Thr Ala Val Val Asn Val Thr Tyr Ser Asn
        115                 120                 125

Arg Glu Gln Thr Arg Gln Ala Ile Met Lys Leu Asn Gly His Gln Leu
    130                 135                 140

Glu Asn His Ala Leu Lys Val Ser Tyr Ile Pro Asp Glu Gln Ile Thr
145                 150                 155                 160

Gln Gly Pro Glu Asn Gly Arg Arg Gly Gly Phe Gly Ser Arg Gly Gln
                165                 170                 175

Pro Arg Gln Gly Ser Pro Val Ala Ala Gly Ala Pro Ala Lys Gln Gln
            180                 185                 190

Pro Val Asp Ile Pro Leu Arg Leu Val Pro Thr Gln Tyr Val Gly
            195                 200                 205

Ala Ile Ile Gly Lys Glu Gly Ala Thr Ile Arg Asn Ile Thr Lys Gln
    210                 215                 220

Thr Gln Ser Lys Ile Asp Val His Arg Lys Glu Asn Ala Gly Ala Ala
225                 230                 235                 240

Glu Lys Ala Ile Ser Val His Ser Thr Pro Glu Gly Cys Ser Ser Ala
                245                 250                 255

Cys Lys Met Ile Leu Glu Ile Met His Lys Glu Ala Lys Asp Thr Lys
            260                 265                 270

Thr Ala Asp Glu Val Pro Leu Lys Ile Leu Ala His Asn Asn Phe Val
    275                 280                 285

Gly Arg Leu Ile Gly Lys Glu Gly Arg Asn Leu Lys Lys Val Glu Gln
290                 295                 300

Asp Thr Glu Thr Lys Ile Thr Ile Ser Ser Leu Gln Asp Leu Thr Leu
305                 310                 315                 320

Tyr Asn Pro Glu Arg Thr Ile Thr Val Lys Gly Ala Ile Glu Asn Cys
                325                 330                 335

Cys Arg Ala Glu Gln Glu Ile Met Lys Lys Val Arg Glu Ala Tyr Glu
            340                 345                 350

Asn Asp Val Ala Ala Met Ser Leu Gln Ser His Leu Ile Pro Gly Leu
    355                 360                 365

Asn Leu Ala Ala Val Gly Leu Phe Pro Ala Ser Ser Ser Ala Val Pro
370                 375                 380
```

```
Pro Pro Pro Ser Ser Val Thr Gly Ala Ala Pro Tyr Ser Ser Phe Met
385                 390                 395                 400

Gln Ala Pro Glu Gln Glu Met Val Gln Val Phe Ile Pro Ala Gln Ala
            405                 410                 415

Val Gly Ala Ile Ile Gly Lys Lys Gly Gln His Ile Lys Gln Leu Ser
            420                 425                 430

Arg Phe Ala Ser Ala Ser Ile Lys Ile Ala Pro Glu Thr Pro Asp
        435                 440                 445

Ser Lys Val Arg Met Val Val Ile Thr Gly Pro Pro Glu Ala Gln Phe
    450                 455                 460

Lys Ala Gln Gly Arg Ile Tyr Gly Lys Leu Lys Glu Glu Asn Phe Phe
465                 470                 475                 480

Gly Pro Lys Glu Glu Val Lys Leu Glu Thr His Ile Arg Val Pro Ala
            485                 490                 495

Ser Ala Ala Gly Arg Val Ile Gly Lys Gly Gly Lys Thr Val Asn Glu
            500                 505                 510

Leu Gln Asn Leu Thr Ala Ala Glu Val Val Pro Arg Asp Gln Thr
        515                 520                 525

Pro Asp Glu Asn Asp Gln Val Ile Val Lys Ile Ile Gly His Phe Tyr
    530                 535                 540

Ala Ser Gln Met Ala Gln Arg Lys Ile Arg Asp Ile Leu Ala Gln Val
545                 550                 555                 560

Lys Gln Gln His Gln Lys Gly Gln Ser Asn Leu Ala Gln Ala Arg Arg
                565                 570                 575

Lys

<210> SEQ ID NO: 3
<211> LENGTH: 14
<212> TYPE: PRT
<213> ORGANISM: Mus musculus

<400> SEQUENCE: 3

Arg Arg Gly Gly Phe Gly Ser Arg Gly Gln Pro Arg Gln Gly
 1               5                   10

<210> SEQ ID NO: 4
<211> LENGTH: 14
<212> TYPE: PRT
<213> ORGANISM: Homo sapiens

<400> SEQUENCE: 4

Gly Arg Arg Gly Leu Gly Gln Arg Gly Ser Ser Arg Gln Gly
 1               5                   10

<210> SEQ ID NO: 5
<211> LENGTH: 14
<212> TYPE: PRT
<213> ORGANISM: Homo sapiens

<400> SEQUENCE: 5

Gly Arg Gly Gly Phe Asp Arg Met Pro Pro Gly Arg Gly Gly
 1               5                   10

<210> SEQ ID NO: 6
<211> LENGTH: 13
<212> TYPE: PRT
<213> ORGANISM: Homo sapiens
```

```
<400> SEQUENCE: 6

Gly Arg Gly Gly Phe Gly Asp Arg Gly Gly Arg Gly Gly
 1               5                  10

<210> SEQ ID NO: 7
<211> LENGTH: 14
<212> TYPE: PRT
<213> ORGANISM: Homo sapiens

<400> SEQUENCE: 7

Gly Arg Gly Gly Phe Gly Gly Arg Gly Gly Gly Arg Gly Gly
 1               5                  10

<210> SEQ ID NO: 8
<211> LENGTH: 14
<212> TYPE: PRT
<213> ORGANISM: Homo sapiens

<400> SEQUENCE: 8

Leu Arg Arg Gly Asp Gly Arg Arg Gly Gly Gly Arg Gly
 1               5                  10

<210> SEQ ID NO: 9
<211> LENGTH: 13
<212> TYPE: PRT
<213> ORGANISM: Artificial Sequence
<220> FEATURE:
<223> OTHER INFORMATION: Consensus sequence for SEQ ID NOs:3-8.

<400> SEQUENCE: 9

Gly Arg Gly Gly Phe Gly Arg Gly Gly Gly Arg Gly Gly
 1               5                  10

<210> SEQ ID NO: 10
<211> LENGTH: 11
<212> TYPE: PRT
<213> ORGANISM: Mus musculus

<400> SEQUENCE: 10

Gln Leu Arg Trp Glu Val Leu Asp Ser Leu Leu
 1               5                  10

<210> SEQ ID NO: 11
<211> LENGTH: 11
<212> TYPE: PRT
<213> ORGANISM: Homo sapiens

<400> SEQUENCE: 11

His Leu Gln Trp Glu Val Leu Asp Ser Leu Leu
 1               5                  10

<210> SEQ ID NO: 12
<211> LENGTH: 10
<212> TYPE: PRT
<213> ORGANISM: Homo sapiens

<400> SEQUENCE: 12

Gln Leu Arg Leu Glu Arg Leu Gln Ile Asp
 1               5                  10

<210> SEQ ID NO: 13
<211> LENGTH: 11
<212> TYPE: PRT
<213> ORGANISM: Homo sapiens
```

```
<400> SEQUENCE: 13

Thr Ile Ser Ser Leu Gln Asp Leu Thr Leu Tyr
 1               5                  10

<210> SEQ ID NO: 14
<211> LENGTH: 11
<212> TYPE: PRT
<213> ORGANISM: Homo sapiens

<400> SEQUENCE: 14

Thr Ile Ser Pro Leu Gln Glu Leu Thr Leu Tyr
 1               5                  10

<210> SEQ ID NO: 15
<211> LENGTH: 11
<212> TYPE: PRT
<213> ORGANISM: Human immunodeficiency virus

<400> SEQUENCE: 15

Gln Leu Pro Pro Leu Glu Arg Leu Thr Leu Asp
 1               5                  10

<210> SEQ ID NO: 16
<211> LENGTH: 7
<212> TYPE: PRT
<213> ORGANISM: Artificial Sequence
<220> FEATURE:
<223> OTHER INFORMATION: Consensus sequence for SEQ ID NOs: 10-15.

<400> SEQUENCE: 16

Gln Leu Leu Glu Leu Thr Leu
 1               5

<210> SEQ ID NO: 17
<211> LENGTH: 47
<212> TYPE: PRT
<213> ORGANISM: Mus musculus

<400> SEQUENCE: 17

Leu Leu Val Pro Thr Gln Tyr Val Gly Ala Ile Ile Gly Lys Glu Gly
 1               5                  10                  15

Ala Thr Ile Arg Asn Ile Thr Lys Gln Thr Gln Ser Lys Ile Asp Val
             20                  25                  30

His Arg Lys Glu Asn Ala Gly Ala Ala Glu Lys Ala Ile Ser Val
         35                  40                  45

<210> SEQ ID NO: 18
<211> LENGTH: 49
<212> TYPE: PRT
<213> ORGANISM: Mus musculus

<400> SEQUENCE: 18

Ile Leu Ala His Asn Asn Phe Val Gly Arg Leu Ile Gly Lys Glu Gly
 1               5                  10                  15

Arg Asn Leu Lys Lys Val Glu Gln Asp Thr Glu Thr Lys Ile Thr Ile
             20                  25                  30

Ser Ser Leu Gln Asp Leu Thr Leu Tyr Asn Pro Glu Arg Thr Ile Thr
         35                  40                  45

Val

<210> SEQ ID NO: 19
<211> LENGTH: 47
```

```
<212> TYPE: PRT
<213> ORGANISM: Mus musculus

<400> SEQUENCE: 19

Val Phe Ile Pro Ala Gln Ala Val Gly Ala Ile Ile Gly Lys Lys Gly
 1               5                  10                  15

Gln His Ile Lys Gln Leu Ser Arg Phe Ala Ser Ala Ser Ile Lys Ile
            20                  25                  30

Ala Pro Pro Glu Thr Pro Asp Ser Lys Val Arg Met Val Val Ile
        35                  40                  45

<210> SEQ ID NO: 20
<211> LENGTH: 48
<212> TYPE: PRT
<213> ORGANISM: Mus musculus

<400> SEQUENCE: 20

Ile Arg Val Pro Ala Ser Ala Ala Gly Arg Val Ile Gly Lys Gly Gly
 1               5                  10                  15

Lys Thr Val Asn Glu Leu Gln Asn Leu Thr Ala Ala Glu Val Val Val
            20                  25                  30

Pro Arg Asp Gln Thr Pro Asp Glu Asn Asp Gln Val Ile Val Lys Ile
        35                  40                  45

<210> SEQ ID NO: 21
<211> LENGTH: 47
<212> TYPE: PRT
<213> ORGANISM: Homo sapiens

<400> SEQUENCE: 21

Leu Leu Val Pro Thr Gln Phe Val Gly Ala Ile Ile Gly Lys Lys Gly
 1               5                  10                  15

Ala Thr Ile Arg Asn Ile Thr Lys Gln Thr Gln Ser Lys Ile Asp Val
            20                  25                  30

His Arg Lys Glu Asn Ala Gly Ala Ala Glu Lys Ser Ile Thr Ile
        35                  40                  45

<210> SEQ ID NO: 22
<211> LENGTH: 49
<212> TYPE: PRT
<213> ORGANISM: Homo sapiens

<400> SEQUENCE: 22

Ile Leu Ala His Asn Asn Pro Val Gly Arg Leu Ile Gly Lys Glu Gly
 1               5                  10                  15

Arg Asn Leu Lys Lys Ile Glu Gln Asp Thr Asp Thr Lys Ile Thr Ile
            20                  25                  30

Ser Pro Leu Gln Glu Leu Thr Leu Tyr Asn Pro Glu Arg Thr Ile Thr
        35                  40                  45

Val

<210> SEQ ID NO: 23
<211> LENGTH: 47
<212> TYPE: PRT
<213> ORGANISM: Homo sapiens

<400> SEQUENCE: 23

Gln Phe Ile Pro Ala Leu Ser Val Gly Ala Ile Ile Gly Lys Gln Gly
 1               5                  10                  15
```

-continued

Gln His Ile Lys Gln Leu Ser Arg Phe Ala Gly Ala Ser Ile Lys Ile
                20                  25                  30

Ala Pro Ala Glu Ala Pro Asp Ala Lys Val Arg Met Val Ile Ile
        35                  40                  45

<210> SEQ ID NO: 24
<211> LENGTH: 48
<212> TYPE: PRT
<213> ORGANISM: Homo sapiens

<400> SEQUENCE: 24

Ile Arg Val Pro Ser Phe Ala Ala Gly Arg Val Ile Gly Lys Gly Gly
 1               5                  10                  15

Lys Thr Val Asn Glu Leu Gln Asn Leu Ser Ser Ala Glu Val Val Val
                20                  25                  30

Pro Arg Asp Gln Thr Pro Asp Glu Asn Asp Gln Val Val Val Lys Ile
        35                  40                  45

<210> SEQ ID NO: 25
<211> LENGTH: 50
<212> TYPE: PRT
<213> ORGANISM: Homo sapiens

<400> SEQUENCE: 25

Ile Leu Leu Gln Ser Lys Asn Ala Gly Ala Val Ile Gly Lys Gly Gly
 1               5                  10                  15

Lys Asn Ile Lys Ala Leu Arg Thr Asp Tyr Asn Ala Ser Val Ser Val
                20                  25                  30

Pro Asp Ser Ser Gly Pro Glu Arg Ile Leu Ser Ile Ser Ala Asp Ile
        35                  40                  45

Glu Thr
    50

<210> SEQ ID NO: 26
<211> LENGTH: 47
<212> TYPE: PRT
<213> ORGANISM: Homo sapiens

<400> SEQUENCE: 26

Leu Leu Ile His Gln Ser Leu Ala Gly Gly Ile Ile Gly Val Lys Gly
 1               5                  10                  15

Ala Lys Ile Lys Glu Leu Arg Glu Asn Thr Gln Thr Thr Ile Lys Leu
                20                  25                  30

Phe Gln Glu Cys Cys Pro His Ser Thr Asp Arg Val Val Leu Ile
        35                  40                  45

<210> SEQ ID NO: 27
<211> LENGTH: 46
<212> TYPE: PRT
<213> ORGANISM: Homo sapiens

<400> SEQUENCE: 27

Val Thr Ile Pro Lys Asp Leu Ala Gly Ser Ile Ile Gly Lys Gly Gly
 1               5                  10                  15

Gln Arg Ile Lys Gln Ile Arg His Glu Ser Gly Ala Ser Ile Lys Ile
                20                  25                  30

Asp Glu Pro Leu Glu Gly Ser Glu Asp Arg Ile Ile Thr Ile
        35                  40                  45

```
<210> SEQ ID NO: 28
<211> LENGTH: 44
<212> TYPE: PRT
<213> ORGANISM: Homo sapiens

<400> SEQUENCE: 28

Phe Ile Val Arg Glu Asp Leu Met Gly Leu Ala Ile Gly Thr His Gly
 1               5                  10                  15

Ala Asn Ile Gln Gln Ala Arg Lys Val Pro Gly Val Thr Ala Ile Asp
            20                  25                  30

Leu Asp Glu Asp Thr Cys Thr Phe His Ile Tyr Gly
        35                  40

<210> SEQ ID NO: 29
<211> LENGTH: 43
<212> TYPE: PRT
<213> ORGANISM: Homo sapiens

<400> SEQUENCE: 29

Ile Gln Val Pro Arg Asn Leu Val Gly Lys Val Ile Gly Lys Asn Gly
 1               5                  10                  15

Lys Leu Ile Gln Glu Ile Val Asp Lys Ser Gly Val Val Arg Val Arg
            20                  25                  30

Ile Glu Ala Glu Asn Glu Lys Asn Val Pro Gln
        35                  40

<210> SEQ ID NO: 30
<211> LENGTH: 18
<212> TYPE: PRT
<213> ORGANISM: Artificial Sequence
<220> FEATURE:
<223> OTHER INFORMATION: Consensus sequence for SEQ ID NOs: 17-29.

<400> SEQUENCE: 30

Leu Leu Val Gly Leu Ile Gly Lys Gly Gly Leu Lys Leu Leu Leu Arg
 1               5                  10                  15

Ile Ile

<210> SEQ ID NO: 31
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 31
gtbaaygary tbcaraa                                                17

<210> SEQ ID NO: 32
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 32
ggvacvacva cytcdgc                                                17

<210> SEQ ID NO: 33
<211> LENGTH: 17
<212> TYPE: DNA
<213> ORGANISM: Artificial Sequence
<220> FEATURE:
<223> OTHER INFORMATION: Oligonucleotide primer
```

-continued

```
<400> SEQUENCE: 33
gctgccgtca aattctg                                                  17

<210> SEQ ID NO: 34
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 34
tcgacggttt ccatatg                                                  17

<210> SEQ ID NO: 35
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 35
aacccggctc gagcggccgc tttttttttt tttttttt                           38

<210> SEQ ID NO: 36
<211> LENGTH: 23
<212> TYPE: DNA
<213> ORGANISM: Artificial Sequence
<220> FEATURE:
<223> OTHER INFORMATION: Oligonucleotide primer

<400> SEQUENCE: 36
acggcagctg aggtggtagt acc                                           23

<210> SEQ ID NO: 37
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 37
aacccggctc gagcggccgc t                                             21

<210> SEQ ID NO: 38
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 38
aggttccgtc cttccttgcc aatg                                          24

<210> SEQ ID NO: 39
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 39
aacttcatct gccgttttgg                                               20

<210> SEQ ID NO: 40
<211> LENGTH: 19
```

```
<212> TYPE: DNA
<213> ORGANISM: Artificial Sequence
<220> FEATURE:
<223> OTHER INFORMATION: Oligonucleotide primer

<400> SEQUENCE: 40
catcaactgg agaaccatg                                                    19

<210> SEQ ID NO: 41
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 41
gactgcgtct gttttgtgat g                                                 21

<210> SEQ ID NO: 42
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 42
ctgtaggaga tcttgtgctc                                                   20

<210> SEQ ID NO: 43
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 43
cgcaccgcca ccatggacaa gctttacatc gg                                     32

<210> SEQ ID NO: 44
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 44
actgggatct gacccatcct                                                   20

<210> SEQ ID NO: 45
<211> LENGTH: 16
<212> TYPE: PRT
<213> ORGANISM: Mus musculus
<220> FEATURE:
<221> NAME/KEY: PEPTIDE
<222> LOCATION: (8)
<223> OTHER INFORMATION: Xaa where Xaa = Gln or Ile
<220> FEATURE:
<221> NAME/KEY: PEPTIDE
<222> LOCATION: (10)
<223> OTHER INFORMATION: Xaa where Xaa = Lys or Arg
<220> FEATURE:
<221> NAME/KEY: PEPTIDE
<222> LOCATION: (11)
<223> OTHER INFORMATION: Xaa where Xaa = Ile or Lys
<220> FEATURE:
<221> NAME/KEY: PEPTIDE
<222> LOCATION: (12)
<223> OTHER INFORMATION: Xaa where Xaa = Tyr or Gly
<220> FEATURE:
```

```
-continued

<221> NAME/KEY: PEPTIDE
<222> LOCATION: (15)
<223> OTHER INFORMATION: Xaa where Xaa = Ile or Leu

<400> SEQUENCE: 45

Pro Ala Gln Val Gly Ala Ile Xaa Gly Xaa Xaa Xaa Gln Xaa Xaa Lys
  1               5                  10                  15

<210> SEQ ID NO: 46
<211> LENGTH: 14
<212> TYPE: PRT
<213> ORGANISM: Mus musculus

<400> SEQUENCE: 46

Asn Glu Leu Gln Asn Leu Thr Ala Ala Glu Val Val Val Pro
  1               5                  10
```

US 6,255,055 B1

C-MYC CODING REGION DETERMINANT-BINDING PROTEIN (CRD-BP) AND ITS NUCLEIC ACID SEQUENCE

CROSS-REFERENCE TO RELATED APPLICATION

This application claims priority to U.S. provisional application Serial No. 60/077,372 filed Mar. 9, 1998. Serial No. 60/077,372 is incorporated by reference as if herein set forth completely.

STATEMENT REGARDING FEDERALLY SPONSORED RESEARCH OR DEVELOPMENT

This invention was made with United States government support awarded by the following agencies: NIH Grant No(s): CA63676; CA07175; CA23076. The United States has certain rights in this invention.

BACKGROUND OF THE INVENTION

The c-myc protein is a member of the helix-loop-helix/leucine zipper (HLH/LZ)[1] family of transcription factors that forms heterodimers with Max (1–3). In general, trans-activating Myc:Max heterodimers are found in proliferating cells, while trans-repressing Mad:Max heterodimers are found in differentiated cells. The c-myc protein level influences cell proliferation, differentiation, and neoplastic transformation, presumably by affecting the balance between Myc:Max and Mad:Max heterodimers (4). When c-myc protein is overexpressed or is induced at inappropriate times, this balance is perturbed, and cell proliferation and differentiation are disrupted. For example, c-myc overexpression prevents or delays cell differentiation (5, 6). It also blocks serum-starved cells from entering the $G_o$ phase of the cell cycle and instead induces them to undergo apoptosis (7). c-myc overexpression is also implicated in tumor formation in experimental animals and in human patients with Burkitt's lymphoma (8, 9). These and other deleterious consequences of aberrant c-myc expression highlight the importance of understanding all aspects of c-myc gene regulation.

[1]The abbreviations used herein are: HLH/LZ, helix-loop-helix/leucine zipper; AURE, AU-rich element; UTR, untranslated region; CRD, coding region determinant; CRD-BP, coding region determinant-binding protein; DTT, dithiothreitol; EGTA, ethylene glycol bis(2 aminoethyl ether)-N,N' (tetraacetic acid); PMSF, phenylmethyl-sulfonylflouride; S130, post-polysomal supernatant; SDS, sodium dodecyl sulfate; RSW, ribosomal salt wash; PCR, polymerase chain reaction; bp, base pairs; EST, Expressed Sequence Tags; RACE, rapid amplification of cDNA ends; BAC, Bacterial Artificial chromosome; GCG, Genetics Computer Group; IP, immunoprecipitation; mRNP, messenger ribonucleoprotein; hnRNPK, heterogeneous nuclear ribonucleoprotein K; HRP, horseradish peroxidase; HSP-90, heat shock protein-90; MOPS, morpholinepropanesulfonic acid; KH, K homology; ORF, open reading frame; FMR, familial mental retardation; FMRP, FMR RNA-binding protein; hKOC, human KH domain protein overexpressed in human cancer; PAG, polyacrylamide gel; PAGE, polyacrylamide gel electrophoresis; ECL, enhanced chemiluminescent.

The c-myc protein is regulated by phosphorylation, protein:protein interactions, and changes in its half-life (10–12). c-myc mRNA levels are regulated transcriptionally and post-transcriptionally, and changes in c-myc mRNA stability can result in large fluctuations in c-myc protein levels. The c-myc mRNA half-life is normally only 10 to 20 minutes but can be prolonged 3- to 6-fold when necessary. For example, c-myc mRNA is relatively stable in replicating fetal rodent hepatocytes, which produce abundant c-myc mRNA. It is far less stable in non-growing adult hepatocytes, which contain little or no c-myc mRNA (13, 14). However, it is up-regulated and stabilized several-fold when adult hepatocytes replicate following partial hepatectomy (15, 16).

Two cis-acting sequence elements in c-myc mRNA contribute to its intrinsic instability and perhaps also to its post-transcriptional regulation: an AU-rich element (AURE) in the 3'-untranslated region (3'-UTR) and a 180 nucleotide coding region determinant (CRD). The CRD encodes part of the HLH/LZ domain and is located at the 3' terminus of the mRNA coding region. Four observations indicate how the c-myc CRD functions independently of the AURE to affect c-myc mRNA expression. (i) c-myc mRNA lacking its CRD is more stable than wild-type c-myc mRNA (17–20). (ii) The CRD is required for the post-transcriptional down-regulation of c-myc mRNA that occurs when cultured myoblasts fuse to form myotubes (20, 21). (iii) Inserting the c-myc CRD in frame within the coding region of β-globin mRNA destabilizes the normally very stable β-globin mRNA (22). (iv) The c-myc CRD is necessary for up- and down-regulating c-myc mRNA levels in transgenic mice undergoing liver regeneration following partial hepatectomy (13, 15, 16, 23–25). In summary, the c-myc CRD influences c-myc mRNA stability in animals and in cultured cells.

We have investigated c-myc mRNA stability and the function of the CRD using a cell-free mRNA decay system that includes polysomes from cultured cells. The polysomes contain both the substrates (mRNAs) for decay and at least some of the enzymes and co-factors that affect mRNA stability. Polysomes are incubated for different times in an appropriate buffer system, and the decay rates of polysomal mRNAs such as c-myc are monitored by hybridization assays. This system reflects many aspects of mRNA decay in intact cells (26–29). For example, mRNAs that are unstable in cells are also relatively unstable in vitro; mRNAs that are stable in cells are stable in vitro (26). In standard reactions, the polysome-associated c-myc mRNA was degraded rapidly in a 3' to 5' direction, perhaps by an exonuclease (29). An alternative decay pathway became activated when the reactions were supplemented with a 180 nucleotide sense strand competitor RNA corresponding to the c-myc CRD. This CRD RNA induced endonucleolytic cleavage within the c-miyc CRD, resulting in an 8-fold destabilization of c-myc mRNA (30). These effects seemed to be specific for c-myc. Other competitor RNAs did not destabilize c-myc mRNA, and c-myc CRD competitor RNA did not destabilize other mRNAs tested.

Based on these observations, we hypothesized that a protein was bound to the c-myc CRD. We further suggested that this protein shielded the CRD from endonuclease attack, that the CRD competitor RNA titrated the protein off of the mRNA, and that the unprotected c-myc CRD was then attacked by an endonuclease. Consistent with this model, we detected a protein that binds strongly in vitro to a c-myc CRD $^{32}$P-RNA probe (30). This protein, the c-myc coding region determinant-binding protein (CRD-BP), was subsequently purified to homogeneity (31). We then found that the CRD-BP is developmentally regulated, being expressed in fetal and neonatal rats but not in adult animals (32).

SUMMARY OF THE INVENTION

In the Examples below, we report the cloning of the mouse CRD-BP cDNA, a novel member of an RNA-binding protein family. We also show that the CRD-BP can bind to ribosomes in vitro and that most of the CRD-BP in cell extracts is located in the cytoplasm and is associated with polysomes and ribosomes. These observations are consistent with a role for the CRD-BP in shielding polysomal c-myc mRNA from endonucleolytic attack, which means that the CRD-BP helps to preserve c-myc mRNA and allows it to be used to make c-MYC protein. We believe that blocking CRD-BP expression might result in the very rapid destruction of c-myc mRNA and subsequent depletion of c-MYC protein from the cell.

We have also shown that the CRD-BP is abundantly expressed in cancer cell lines grown in the laboratory as well as in fetal tissues from rodents (32). In contrast, the CRD-BP is undetectable in tissues from adult rodents (32). We believe that these latter observations may be consistent with the idea that the CRD-BP is an oncofetal protein—that is, a protein that is expressed in the fetus and in cancer cells in post-natal life but is not expressed in normal (non-cancerous) tissues in post-natal life. If so, then the CRD-BP should be present in cancer tissues but not in normal tissues in post-natal life.

Specific, restricted expression of the CRD-BP in cancerous tissues could mean that the CRD-BP is a potential diagnostic/prognostic marker for human cancer. Moreover, since the CRD-BP seems to protect c-myc mRNA from being destroyed rapidly, and since c-MYC protein is essential for cell growth, then eliminating the CRD-BP from cancer cells could lead to the cessation of their growth or even to their death.

The present invention is a method of diagnosing the presence or absence of cancer in a human patient comprising the steps of examining patient tissue for the CRD-BP expression levels and comparing that expression level with a control or examining patient serum for antibody against the CRD-BP and comparing that antibody level with that of normal controls (preferably age-matched and sex-matched). Preferably, the control for the CRD-BP expression level in tissues is a non-cancerous tissue from the same source as the test tissue. For example, a breast assay would preferably have a breast tissue control. In a preferred embodiment of the present invention, the cancer is selected from the group consisting of breast cancer, colon cancer and pancreatic cancer.

In another preferred embodiment of the present invention, the detection of CRD-BP comprises the step of homogenizing biopsy tissue and obtaining a crude protein extract. One would then examine that extract for the CRD-BP level.

The present invention is also a quantitative method of determining the stage of cancer in a human patient comprising the step of examining patient tissues for the CRD-BP expression level and correlating that expression level with the disease prognosis.

The present invention is also a method of inhibiting cancer cell growth comprising the step of eliminating or lowering the level of CRD-BP in the cancerous cells.

It is an advantage of the present invention that a method of diagnosing human cancers is disclosed.

It is another advantage of the present invention that a method of inhibiting cancer cell growth is disclosed.

Other objects, advantages and features of the present invention will become apparent after one of skill in the art has examined the specification, claims and drawings.

BRIEF DESCRIPTION OF THE SEVERAL VIEWS OF THE DRAWINGS

FIGS. 1A, B, C and D. Mouse CRD-BP cDNA and predicted protein sequence (SEQ ID NOs:1 and 2, respectively). Peptide sequences resembling nuclear localization and nuclear export signals are denoted by the single underline and the overlines, respectively. Peptide sequences resembling the RGG box and the KH domains are denoted by the box and the double underlines, respectively. An asterisk indicates the translation termination site, and the polyadenylation signal is single underlined. We have not demonstrated conclusively that the translation start site indicated in the figure is the correct or the only start site. The 5'-UTR might be incomplete, since the transcription start site has not been mapped.

FIG. 2. CRD-BP alignments with various consensus sequences in RNA binding proteins (SEQ ID NOs:3–30). Shown are alignments of the mouse CRD-BP (mCRD-BP) to the RGG domains (A) (SEQ ID NOs:3–9) nuclear export signals (B) (SEQ ID NOs:10–16), and KH domains (C1 and C2) (SEQ ID NOs:17–30) of other RNA-binding proteins. Referring to FIG. 2, boxed residues indicate identity with or conservation to the consensus sequence residue. The Genbank accession numbers of the proteins are as follows: hKOC, U97188; hnRNPK, S74678; fibrillarin, X56597; nucleolin, M60858/J05584; FMRP, S65791; Rev, X58781.

FIG. 6. Co-fractionation of endogenous CRD-BP with K562 cell polysomes and lack of CRD-BP in nuclei. Subcellular fractions were prepared from exponentially growing K562 cells (Experimental Procedures). Equal cell equivalents ($6 \times 10^5$) of each fraction were separated in a 10% SDS-PAG, transferred to a nitrocellulose membrane, and incubated with either (A) anti-CRD-BP IgY or (B) anti-HSP-90 IgG, followed by incubation with horseradish peroxidase (HRP)-conjugated secondary antibodies. Immunoreactive proteins were visualized using ECL reagents. The positions of molecular mass markers are indicated on the left in kDa.

FIG. 7. Co-fractionation of the CRD-BP with ribosomal subunits from K562 cells. Polysomes from exponentially growing K562 cells were resuspended in buffer and then incubated in 20 mM EDTA to dissociate ribosomal subunits (60S and 40S) from each other and from mRNP. An aliquot of the subunits was centrifuged in a linear 5–30% sucrose gradient containing EDTA. Fraction 1 is the top of the gradient, fraction 18 is the last gradient fraction, and fraction 19 is the pellet resuspended from the bottom of the centrifuge tube. Panel A: absorbance of each fraction at 260 nm. Panel B: RNA isolated from an aliquot of each fraction was electrophoresed in a 1% agarose gel, which was stained with ethidium bromide and photographed under UV light. The positions of the 28S and 18S rRNAs from the large and small ribosomal subunits, respectively, are noted on the left. Panel C: An aliquot of each fraction was analyzed by immunoblotting using anti-CRD-BP IgY. Immunoreactive proteins were visualized using ECL reagents. The positions of molecular mass markers are indicated in kDa on the left. The CRD-BP and the cross-reacting p85 are noted on the right.

DETAILED DESCRIPTION OF THE INVENTION

A. In General

Figure 3:
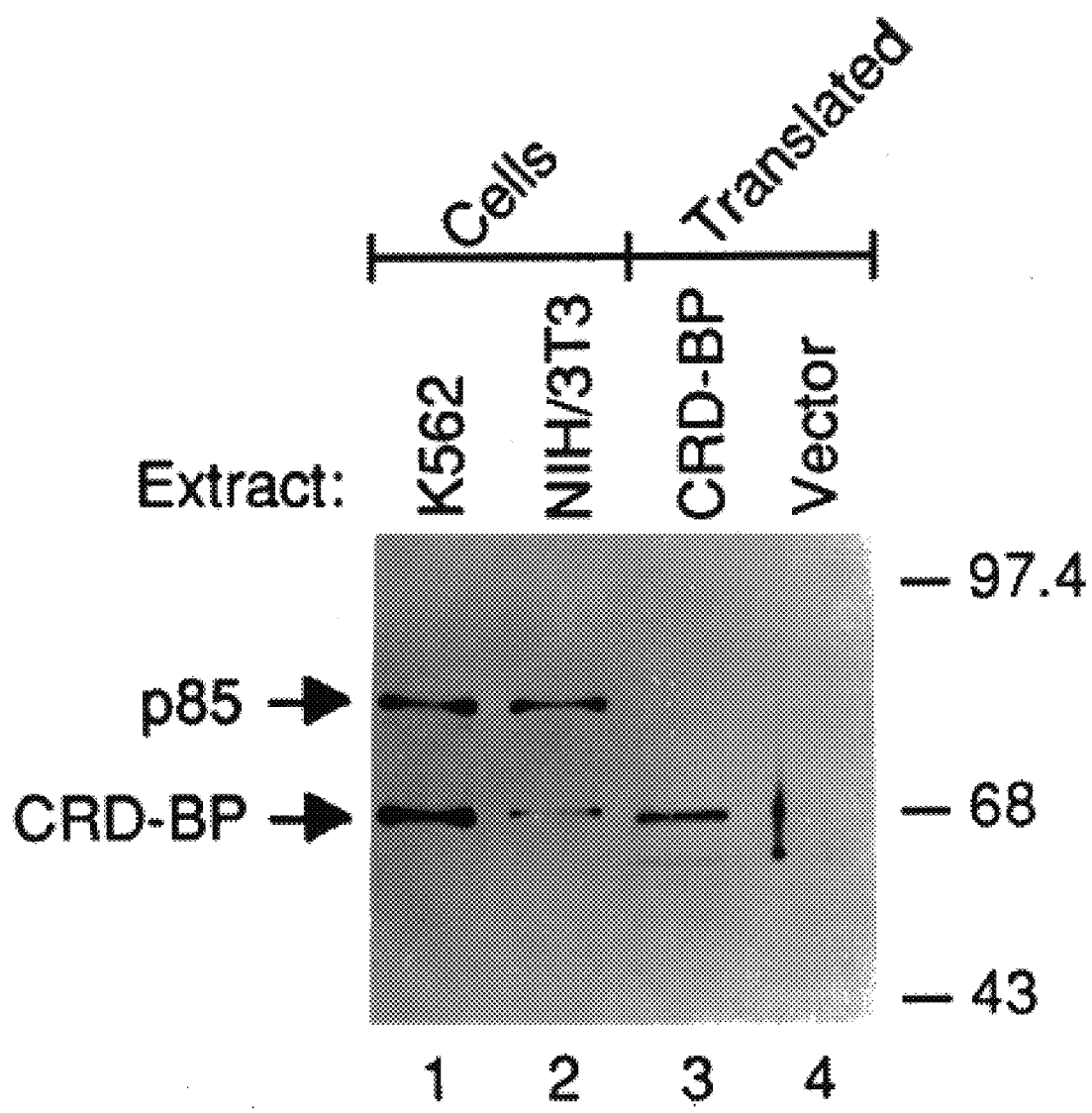
FIG. 3. Immunoblotting assay showing co-migration of recombinant and cell derived CRD-BP. Ribosomal salt wash (RSW) was prepared from K562 and NIH/3T3 cell polysomes and from polysomes isolated from reticulocyte transcription/translation reactions programmed with CRD-BP DNA or with vector DNA. Approximately $7.5 \times 10^5$ cell equivalents of K562 or NIH/3T3 RSW or 3% of the RSW recovered from a 50 $\mu$l translation reaction were electrophoresed in a 10% SDS-PAG and transferred to a membrane, which was incubated with anti-CRD-BP IgY antibody and then with HRP-conjugated anti-IgY antibody. The signal was developed with Supersignal chemiluminescent reagents. The locations of the CRD-BP and a cross-reacting protein (p85) are indicated. The locations of prestained molecular mass markers are shown on the right in kDa.

The half-life of c-myc mRNA is regulated when cells change their growth rates or differentiate. Two sequences within the c-myc mRNA molecule determine its half-life, one in the 3'-untranslated region, the other in the coding region. A cytoplasmic protein, the coding region determinant-binding protein (CRD-BP), binds in vitro to the c-myc coding region stability determinant.

Based on observations using a cell-free mRNA decay system, we propose that the CRD-BP, when bound to the mRNA, shields the mRNA from endonucleolytic attack and thereby prolongs the mRNA half-life. Here we describe the cloning and further characterization of the mouse CRD-BP, a 577 amino acid protein containing four hnRNP K-homology domains, an RGG RNA-binding domain, and nuclear import and export signals. The CRD-BP is similar to a human protein overexpressed in certain human cancers. Recombinant mouse CRD-BP binds specifically to c-myc CRD RNA in vitro and reacts with antibody against human CRD-BP. In vitro translated CRD BP binds to ribosomes in the absence of c-myc mRNA, and much of the CRD-BP in cell lysates is associated with ribosomes.

We also describe below proposed methods for the present invention. In one embodiment, we propose a method of diagnosing the presence or absence of cancer in a human patient comprising the steps of examining patient tissue for the CRD-BP expression levels and comparing that result with a control sample and/or examining patient serum for antibody against the CRD-BP and comparing that antibody level with that of normal controls (preferably age-matched and sex-matched). Preferably, the control sample for the CRD-BP expression level in tissues is a non-cancerous tissue from the same source. For example, one would compare the CRD-BP levels of a test breast tissue sample with the CRD-BP levels of breast tissue known to be non-cancerous.

This examination may take the form of examining a crude protein extract for the CRD-BP level, preferably by two antibody sandwich assay, antigen competition assay, antibody capture assay, or by immunoblotting of the crude protein extract with an antibody to CRD-BP. One may also examine the cells in the tissue samples directly for the presence or absence of CRD-BP via immununological methods involving probing a tissue section with an antibody to CRD-BP or via in situ hybridization methods involving probing a tissue section with a nucleic acid probe specific for the CRD-BP.

In another embodiment, the present invention is a method of determining cancer disease prognosis. One would examine the CRD-BP expression levels in a patient tissue sample and correlate these CRD-BP levels with disease prognosis.

The present invention is also the use of CRD-BP in immunological assays to identify and quantify anti-CRD-BP antibodies in patient sera. Preferably, one would use recombinant CRD-BP in standard immunological assays. The present invention is also the use of anti-CRD-BP antibodies to identify and quantify the CRD-BP itself in serum from cancer patients.

We expect to find that certain expression levels of CRD-BP can be directly correlated with, and are therefore predictive of, certain cancers.

We also propose a method of inhibiting cancer cell growth by eliminating or lowering the level of CRD-BP from the cancerous cells. Preferably, this method is either by providing the cell with competitor RNA or by use of an inhibitor that blocks CRD-BP binding to the c-myc mRNA CRD.

By "CRD-BP" we preferably mean the protein as described herein at SEQ ID NO:2 and in Ref. 30, 31 and 32 below.

One typical way to obtain a CRD-BP antibody would be to make large amounts of recombinant CRD-BP in either bacterial cells, yeast cells or baculovirus-infected insect cells. This protein is then injected into rabbits, sheep or goats to make a polyclonal antibody. Epitope-specific antibodies can also be made by using synthetic peptides (8–15 amino acids) as the immunogen. These are routine techniques known to those of skill in the art.

B. Detecting the CRD-BP in Clinical Samples

We have hypothesized that the CRD-BP might be an oncofetal protein. This hypothesis is based on our findings that the CRD-BP is expressed in fetal rat tissues but not in normal adult rat tissues. It is also expressed in tissue culture cell lines, which are neoplastic.

We show below in the Examples that the CRD-BP is significantly more abundant in tumor tissue than in a normal adult tissue. Therefore, we envision that the presence of the CRD-BP in biopsy specimens indicates that the specimens contain tumor cells. We envision that the presence of the CRD-BP is indicative of neoplasia and would be a prognostic and diagnostic indicator.

There are many possible CRD-BP detection schemes. The best scheme will depend on the following variables: the amount of CRD-BP expressed in the tumor tissue, the specificity and avidity of the antibodies for the CRD-BP, and the extent of cross-reactivity of the antibodies with other proteins besides the CRD-BP. Below is an outline of several possible detection schemes.

It is probably best to ensure that the antibodies are specific for the CRD-BP. We can do so by making antibodies against CRD-BP peptides or by using monoclonal antibodies that, on Western blots, react only with the CRD-BP and not with any other cellular proteins.

1. Detection of the CRD-BP Using Protein Extracts: Biopsy Tissue would be Homogenized and a Crude Protein Extract would be Prepared (Proposed).

a. Exemplary Detection schemes in which antigen or antibody is bound to a solid support.

i. Two antibody sandwich assay: A monoclonal antibody recognizing one CRD-BP epitope is bound to a solid support such as a microtiter well. The sandwich assay would also work with two polyclonal antibodies, as long as each antibody was against a different epitope in the CRD-BP. An extract of the tissue is added, and CRD-BP in the extract is permitted to bind to the antibody. Then a second monoclonal recognizing a different CRD-BP epitope is added. The second antibody can be labeled with $^{125}I$ or $^3H$. Then, the amount of labeled antibody bound will provide a measure of the amount of CRD-BP attached to the first antibody.

Alternatively, a tagged secondary antibody can be used for quantitation. This secondary antibody can be tagged with an enzyme such as horseradish peroxidase or with a probe such as biotin. The amount of bound secondary antibody is then detected by standard assays and is a measure of the amount of CRD-BP in the tissue extract.

ii. Antigen competition assay: Anti-CRD-BP antibody is bound to a solid support such as a microtiter well. The tissue extract is then mixed with purified, radiolabeled CRD-BP. If the tissue contains sufficient CRD-BP, this CRD-BP will compete with the labeled CRD-BP for binding to limiting antibody. Thus, the amount of CRD-BP in the extract will be inversely proportional to the amount of labeled CRD-BP bound to the microtiter well. We know the nucleic acid sequence of the human CRD-BP coding region. Therefore, we should be able to prepare highly purified, radiolabeled CRD-BP using bacteria, yeast, or insect cells.

Prokipcak, et al. (ref. 31) discloses one method of purification of CRD-BP. We also envision an easier purification scheme that exploits added epitopes. Instead of making unmodified CRD-BP in bacteria, yeast, or baculovirus-infected cells, we could use molecular techniques to design a CRD-BP complementary DNA that would generate an "epitope-tagged" CRD-BP. We could express the tagged CRD-BP in cells and then purify the CRD-BP in a single affinity step that exploits the tag to separate CRD-BP from all the other cell proteins.

iii. Antibody capture assay: The tissue extract is bound to a microtiter well. Antibody is added, and the amount of antibody bound is determined. The antibody can be labeled or unlabeled. If it is unlabeled, the amount bound is determined indirectly, using anti-antibody antibodies and detecting them by peroxidase or biotin labeling, as described above.

b. Exemplary Detection of the CRD-BP by Immunoblotting (Western Blotting)

Tissue extract is electrophoresed in a denaturing gel, and the proteins are transferred to a nitrocellulose or PVDF membrane. The membrane is then probed with anti-CRD-BP antibody, and the amount of antibody bound is determined by any of a variety of detection techniques using tagged anti-antibody antibodies. The disadvantage of Western blotting is that it is more time-consuming than assays in which the extract protein or the antibody is bound to a solid support. The advantage is that specific interactions are more readily discerned, and artifacts are eliminated. The presence of the CRD-BP in a Western blot is indicated by a band at the ~68 kilodalton region of the gel.

We envision that the assay might be simplified to the point that a dipstick or calorimetric assay could be used.

2. Detection of CRD-BP in Cells by Immunohistochemistry

In a typical method, the biopsy tissue is cut into a thin section and fixed and then analyzed using standard immunohistochemical techniques. The detection system will depend on the amount of CRD-BP in the tissue. Although this technique is more time-consuming than techniques using tissue extracts, immunohistochemistry can identify rare abnormal cells. For example, a biopsy specimen might contain primarily normal cells with only small patches of neoplastic cells. If the neoplastic cells express the CRD-BP, then they might be visualized by immunohistochemistry using CRD-BP-specific antibodies.

3. Detection of CRD-BP in Cells by in situ Hybridization

In a typical method, the biopsy tissue is cut into a thin section and fixed and then analyzed using standard in situ hybridization techniques with a CRD-BP DNA or RNA probe. As is the case with immunohistochemistry, an advantage of the in situ hybridization technique is the ability to detect rare cancerous cells in the midst of a majority of normal cells.

C. Detecting CRD-BP or CRD-BP Antibodies in Patient Sera

The CRD-BP is a cytoplasmic protein. Therefore, it should not be exposed to immune cells under most conditions. However, if it is overexpressed in human tumor cells, and if these cells undergo lysis or the protein for whatever reason leaks out of the cells, the CRD-BP itself might be detected in patient serum, and/or antibodies to the CRD-BP might arise in patients with tumors. Detecting the CRD-BP or such antibodies in a small amount of patient serum would then provide a rapid and convenient screen for cancer. The previous section outlined methods for detecting the CRD-BP. Strategies to detect anti-CRD-BP antibodies might exploit techniques similar to those for detecting the CRD-BP itself in extracts from biopsy material. There are many ways for detecting antibodies. Some of the techniques that would be suitable for detecting anti-CRD-BP antibodies in patient serum are summarized below.

i. Two Antibody Sandwich Assay

The CRD-BP itself will be made in bacterial, yeast or insect cells using standard techniques. This recombinant CRD-BP will then be bound to a solid support such as a microtiter well. Patient serum is added, and anti-CRD-BP antibody in the serum is permitted to bind to the CRD-BP. The plates are then washed extensively, and a second anti-human serum is added. The second antibody can be labeled with 125I or 3H or with a fluorescent tag. Then, the amount of labeled antibody bound will provide a measure of the amount of anti-CRD-BP antibody attached to the recombinant CRD-BP on the plate. Alternatively, a tagged secondary antibody can be used for quantitation. This secondary antibody can be tagged with an enzyme such as horseradish peroxidase or with a probe such as biotin. The amount of bound secondary antibody is then detected by standard assays and is a measure of the amount of anti-CRD-BP antibody in the serum of the patient.

ii. Antigen Capture Assay

Serum from the patient is attached to a solid support such as a microtiter well. Then radiolabeled, recombinant CRD-BP is added. Unbound CRD-BP is washed off of the plate, and the amount of bound antigen is measured. The radiolabeled CRD-BP could be labeled in vivo in bacteria or yeast using 35S or could be radioiodinated in vitro.

D. Treatment of Cancer by Eliminating the CRD-BP from the Cancer Cells

The basic idea of the present invention is primarily based on two notions: that the CRD-BP stabilizes c-myc mRNA in cells and that the CRD-BP is expressed post-naturally in tumor cells but not in normal cells. As a result, c-myc mRNA is overexpressed or inappropriately expressed in tumor cells. If the CRD-BP could be eliminated, then c-myc mRNA would be destabilized. If c-myc mRNA were essential for growth or viability of the tumor cells, then the tumor cells would stop growing or die. Selectivity would be assured if the CRD-BP were expressed more abundantly in tumor cells.

Two approaches are preferred for interfering with the interaction of the CRD-BP with c-myc mRNA:

1. Genetic Engineering

The way we destabilized c-myc mRNA in our cell-free mRNA decay system was to add excess competitor RNA to the reactions. The RNA contains the 180 nucleotides of the c-myc mRNA coding region determinant (CRD). The competitor RNA is thought to titrate the CRD-BP from c-myc mRNA. As a result, the CRD of c-myc mRNA is not shielded by the CRD-BP, and the mRNA is rapidly degraded by a ribonuclease.

In order to exploit a similar strategy in intact cells, it would be necessary to apply the techniques of genetic engineering to overexpress c-myc mRNA CRD RNA in the affected tissue or organ. One might introduce DNA capable of expressing the CRD competitor RNA in the tissue or organ. Alternatively, it might be feasible to introduce a ribonuclease-resistant, long-lasting form of CRD RNA itself. It is important to note that specificity would be achieved if the target cancer cells were expressing the CRD-BP, while non-cancer cells did not express it. Under these conditions, the competitor CRD RNA would have a deleterious effect only on the cancer cells.

2. Use of an Inhibitor that Blocks CRD-BP Binding to the c-myc mRNA CRD

We presume that the CRD-BP folds in such a way that it is able to recognize a particular segment of c-myc mRNA, namely, the CRD RNA segment. One could design peptide or nucleic acid analogues or other compounds that bind to the CRD-BP so as to inhibit its ability to interact with c-myc mRNA in cells. This is similar to strategies that are being considered by pharmaceutical companies hoping to design antiviral compounds capable of entering cells and interacting with viral-derived proteins and nucleic acids. The protease inhibitors used in HIV-infected patients are an example of a pharmaceutical agent directed against a specific viral-encoded product.

EXAMPLES

A. Experimental Procedures Cell lines and preparation of subcellular fractions.

All cell lines were obtained from the American Type Culture Collection (Rockville, Md.). K562 human erythroleukemia cells were cultured in RPMI-1640 medium containing 10% calf serum plus a penicillin/streptomycin mix. NIH/3T3 cells were grown in DMEM (4.5 g/L glucose) containing 10% calf serum and antibiotics. All antibiotics and sera were from Gibco/BRL Life Technologies.

Subcellular fractions were prepared as follows. All steps following cell harvesting were at 4° C. Cells were grown in 1 liter spinner flasks to a density of $3-5 \times 10^5$ cells/ml. They were harvested, collected by low speed centrifugation, and washed 3 times with cold F12 medium without serum. The cell pellet was resuspended at a density of $1.5 \times 10^7$ cells/ml in Buffer A (1 mM potassium acetate, 1.5 mM magnesium acetate, 2 mM DTT, 10 mM Tris-Cl, pH 7.4) containing 100 mM EGTA, 100 mg/ml PMSF, and 2 mg/ml each of aprotinin, leupeptin, and pepstatin A (all from Sigma). The cells were lysed with 30–40 strokes of a Dounce homogenizer, and the lysate was centrifuged for 10 minutes at 20,000×g to pellet nuclei and other organelles. The supernatant (S20) was layered over a cushion of 30% (w/v) sucrose dissolved in Buffer A and was centrifuged for 2.5 hours at 130,000×g to pellet polysomes. The supernatant (S130) above the sucrose cushion was harvested, and the polysomal pellet was resuspended in Buffer A containing PMSF, leupeptin, pepstatin A, and aprotinin. The S20 pellet (crude nuclei) was washed once in Buffer A and centrifuged, and the nuclear wash material in the supernatant was harvested and saved. The pelleted, washed nuclei were then resuspended in 300 μl of Buffer B (1.5 mM MgCl2, 140 mM NaCl, 20% glycerol, 10 mM Tris-Cl, pH 8.0) and lysed by adding 2.7 ml of Buffer C (5.0% SDS, 10% glycerol, 5% β-mercaptoethanol, 62.5 mM Tris-Cl, pH 6.8). The extract was then passed 10 times through an 18-gauge needle and boiled for 15 minutes. To isolate ribosomal salt wash (RSW) from either tissue culture cells or reticulocyte translation reactions, an aliquot of polysomes was incubated for 20 minutes at 4° C. with 1 M NaCl in buffer A, followed by centrifugation for 2.5 hours at 130,000×g to re-pellet the salt washed polysomes (26). Glycerol was added to 10% to the supernatant (RSW) above the sucrose cushion, and the salt-washed polysomes were resuspended in Buffer A containing the protease inhibitors. All fractions were stored at −70° C.

Protein purification and microsequencing. The human c-myc CRD-BP was purified from K562 cell RSW as described (31). Two independent preparations of CRD-BP from different RSW isolates were microsequenced for this study. The first sequence was determined at the Protein Sequence and Peptide Synthesis Facility of the University of Wisconsin Biotechnology Center (Madison, Wis.). The second sequence was distinct from the first, did not overlap, and was determined at the Keck Laboratories, Yale University (New Haven, Conn.). The second sequence was used for preparing PCR primers.

Cloning of Mouse CRD-BP cDNA.

1. CRD-BP cDNA cloning. We first prepared a human CRD-BP cDNA and used its sequence to identify mouse CRD-BP cDNA. DNA oligomers were synthesized by the Nucleic Acid Sequence and Oligomer Synthesis Facility of the University of Wisconsin Biotechnology Center (Madison, Wis.) or by GIBCO-BRL Life Technologies (Grand Island, N.Y.). A K562 (human) cell cDNA lambda library (Clontech, Palo Alto, Calif.) was first screened by degenerate PCR in order to amplify a 45 bp DNA sequence based on the 15 amino acids of the second CRD-BP peptide sequence. The following primers were used: 5'-GTBAAYGARYTBCARAA-3' (coding) (SEQ ID NO:31) and 5'-GGVACVACVACYTCDGC-3' (non-coding)

(SEQ ID NO:32). The conditions were 30 cycles, 94° C. for 30 seconds, 45° C. for 30 seconds, 72° C. for 1 minute, AMPLITAQ DNA Polymerase (Perkin Elmer). PCR products from this and subsequent reactions were subcloned directly into pT7-Blue (Novagen, Madison, Wis.) for sequencing, which was performed by PCR using the ABI Prism AmpliTaq FS Dye Terminator Reaction Kit (Applied Biosystems, Inc.) according to the manufacturer's recommendations. A 45 bp product encoding the expected 15 amino acid sequence was isolated in this way. The same cDNA library was then used for non degenerate PCR with a CRD-BP-specific coding primer from the middle of the 45 bp sequence (5'-GCTGCCGTCAAATTCTG-3') (SEQ ID NO:33) plus a lambda-specific primer (5'-TCGACGGTTTCCATATG-3') (SEQ ID NO:34) under the following conditions: 30 cycles, 94° C. for 30 seconds, 50° C. for 30 seconds, 72° C. for 3 minutes, AMPLITAQ DNA Polymerase. This step generated a 227 bp cDNA. The same library was then plated, transferred in duplicate to nitrocellulose filters, and screened by hybridization with the 227 bp $^{32}$P-DNA as probe. This step generated a 1069 bp partial human CRD-BP cDNA with an open reading frame encoding both of the peptides obtained by sequencing purified CRD-BP. This cDNA did not contain the 5' part of the coding region, the 5'-UTR, or most of the 3'-UTR.

To complete the cloning of the 3' terminal region 3' rapid amplification of cDNA ends (3'-RACE) was performed. Oligomer Not(dT) (5'-AACCCGGCTCGAGCGGCCGC TTTTTTTTTTTTTTTTT-3') (SEQ ID NO:35) and Superscript II (GIBCO-BRL) were used according to the manufacturer's recommendations to reverse transcribe 0.5 µg of K562 cell poly(A)+mRNA. The cDNA template was then amplified using VENT DNA Polymerase (New England Biolabs) with oligomers CRD-BP1 (5' ACGGCAGCTGAGGTGGTAGTACC-3') (SEQ ID NO:36) and NotAdaptmer (5'-AACCCGGCTCGAGCGGCCGCT-3') (SEQ ID NO:37) as 5' and 3' primers, respectively. Conditions were 1 cycle of 94° C. for 1 minute, followed by 35 cycles of 94° C. for 30 seconds, 60° C. for 30 seconds, 72° C. for 1.5 minutes.

2. Cloning of mouse CRD-BP cDNA. The partial human CRD-BP CDNA generated as described above was used to identify mouse CRD-BP cDNAs in the EST Database using the NCBI Blast Program. The larger of the two EST's, AA073514, was obtained from Genome Systems, Inc. (St. Louis, Mo.) and was sequenced. The amino acid sequence it encoded was 99% identical to that of our human CRD-BP, indicating that it corresponded to the mouse CRD-BP. It contained the entire 3'-UTR and most of the coding region. To extend the 5' sequence, 5'- RACE was performed on a 17 day mouse embryo Marathon-Ready cDNA Library (Clontech) using ADVANTAGE KlenTaq DNA Polymerase (Clontech) according to the manufacturer's instructions. In primary reactions, "touchdown PCR" was performed with oligomers AP1 (Clontech) and CRD-BP2 (5'-AGGTTCCGTCCTTCCTTGCCAATG-3') (SEQ ID NO:38) as 5' and 3' primers, respectively. Conditions were 1 cycle of 94° C. for 1 minutes, 5 cycles of 94° C. for 10 seconds, 72° C. for 7.5 minutes, 5 cycles of 94° C. for 10 seconds, 70° C. for 7.5 minutes, 20 cycles of 94° C. for 10 seconds, 68° C. for 7.5 minutes, 10 cycles of 94° C. for 10 seconds, 60° C. for 20 seconds, 68° C. for 7.5 minutes. DNA bands were excised from a 1% agarose gel, and secondary PCR was performed with them using nested 5' and 3' primers [oligomers AP2 (Clontech) and CRD-BP3 (5'-AACTTCATCTGCCGTTTTGG 5') (SEQ ID NO:39), respectively]. Conditions were 1 cycle of 94° C. for 1 minutes, followed by 25 cycles of 94° C. for 15 second, 60° C. for 30 seconds, 68° C. for 5 minutes. Since the resulting clone did not contain the translation start site or any 5'-UTR, a mouse BAC library was screened for the CRD BP gene by PCR with primers CRD-BP4 (5'-CATCAACTGGAGAACCATG-3') (SEQ ID NO:40) and CRD-BP5 (5'-GACTGCGTCTGTTTTGTGATG-3') (SEQ ID NO:41). A BAC clone containing the mouse CRD-BP gene was obtained from Genome Systems. The remainder of the coding region and at least part of the 5'UTR was sequenced from this BAC clone using oligomer CRD BP6 (5'-CTGTAGGAGATCTTGTGCTC-3') (SEQ ID NO:42) as primer. Sequence comparisons were generated using the Genetics Computer Group (GCG) Bestfit and Gap algorithms. Theoretical translations were made with the GCG Translate program.

In vitro translation of mouse CRD-BP. A portion of the mouse CRD-BP cDNA was subcloned into pSPUTK (Stratagene, La Jolla, Calif.) to create the translation clone pSPUTK-CRD-BP as follows: A single base mutation (underlined) was made in the 5' primer (5° CGCACCGCCACCATGGACAAGCTTTACATCGG-3') (SEQ ID NO:43) to generate an NcoI site for subcloning. The mutation changes an asparagine to an aspartic acid. The 3' primer (5'-ACTGGGATCTGACCCATCCT-3') (SEQ ID NO:44) was from the CRD-BP 3'-UTR. Conditions were 1 cycle of 94° C. for 1 minute, followed by 25 cycles of 94° C. for 30 seconds, 55° C. for 30 seconds, 68° C. for 3 minutes. pSPUTK-CRD-BP, pSPUTK-Luciferase, or pSPUTK vector templates were transcribed and translated using the TnT® Coupled Reticulocyte Lysate System (Promega) according to the manufacturer's instructions.

Immunoprecipitation, immunoblotting, and gel retardation assays. Immunoprecipitation (IP) of 60S ribosomal subunits was performed essentially as previously described (33). Briefly, human anti-P protein serum (Immunovision) or normal human serum was conjugated to Protein G-Plus Sepharose beads (Oncogene Science). The anti-P protein serum recognizes three large ribosomal subunit proteins ($P_0$-38 kDa, $P_1$-19 kDa, $P_2$-17 kDa; ref. 34). K562 polysomes were dissociated into mRNP and ribosomal subunits by incubation with 20 mM EDTA at 4° C. for 20 minutes. Protein G-Plus Sepharose-conjugated antibodies were then incubated with 10 µl of the dissociated polysomes in IP buffer (100 mM KCl, 5 mM EDTA, 1 mM DTT, 0.5% Triton X-100, 100 µg/ml PMSF, 0.5% aprotinin, and 2 µg/ml each leupeptin and pepstatin A, 10 mM HEPES, pH 7.3) for 16 hours at 4° C. with gentle mixing. The beads were washed three times for 20 minutes each at 4° C. in IP buffer. Bound proteins were eluted by resuspending the beads in Buffer D (2.3% SDS, 10% glycerol, 62.5 mM Tris-Cl, pH 6.8) and incubating the beads at 95° C. for 5 minutes.

Immunoblotting was performed as previously described (32). For CRD-BP, the primary antibody was a chicken anti-CRD-BP IgY raised against the purified human protein (31, 32), and the secondary detection antibody was horseradish peroxidase (HRP) conjugated rabbit anti-chicken IgY (Promega). For the ribosomal P proteins, human anti-P protein serum (see above) was the primary antibody, and the secondary detection antibody was HRP-conjugated goat anti-human IgG (Promega). For heat shock protein-90 (HSP 90), the primary antibody was a rabbit anti-mouse HSP-90 polyclonal IgG (a kind gift from Dr. Alan Poland), and the secondary detection antibody was HRP-conjugated goat anti-rabbit IgG (Sigma). Blots were developed by enhanced chemiluminescence (ECL) using either standard (Amersham) or Supersignal ULTRA (Pierce) reagents. Distinct bands were not detected with preimmune antibodies, normal human serum, or secondary antibodies alone (data not shown). Where noted, blots were stripped for 30 minutes at 50° C. in 2% SDS, 100 mM β-mercaptoethanol, 50 mM K2HPO4, pH 6.8 and were then washed extensively in buffer containing 5% nonfat dry milk to remove SDS and β-mercaptoethanol. Gel retardation assays were performed as previously described (31, 32).

Sucrose gradient centrifugation and ribosomal RNA analysis. All procedures were performed at 4° C. For analyzing the CRD-BP association with ribosomal subunits, an aliquot of K562 cell polysomes (50 µl) or cytoplasmic lysate (S20; 150 µl) was brought to a final concentration of 20 mM EDTA. The material was mixed gently, left on ice for 20 minutes, layered over a 10 ml linear 5–30% sucrose gradient in Buffer E (100 mM KCl, 10 mM potassium acetate, 5 mM EDTA, 1 mM DTT, 5 mM HEPES, pH 7.3) (33), and centrifuged in a Beckman SW41.1 rotor for 4 hours at 4° C., 38,000 rpm (178,000×g). Following centrifugation, 500 µl fractions were pipetted sequentially from the top of the gradient. The pellet at the bottom of the tube was resuspended in 500 µl of Buffer E containing 5% sucrose. Proteins were precipitated with methanol and chloroform prior to immunoblotting. RNA from each fraction was isolated using TRIzol reagent (Gibco/BRL) following the manufacturer's directions and was electrophoresed in a 1% agarose gel containing 10 mM sodium acetate, 1 mM EDTA, 40 mM MOPS, pH 7.0. Ribosomal RNA bands were visualized by staining with ethidium bromide (0.05 µg/ml).

Recombinant, 35S-labeled CRD-BP or luciferase was synthesized in reticulocyte extracts and analyzed by sucrose gradient centrifugation essentially as previously described (35) with slight modifications. The reactions (100 µl) were chilled on ice, layered over a 4 ml linear 20–40% sucrose gradient containing 25 mM potassium acetate, 1.5 mM magnesium acetate, 1 mM DTT, 20 mM Tris-Cl, pH 7.2, and centrifuged in a Beckman SW60 rotor for 5 hours at 4° C., 133,000×g. Fractions were pipetted sequentially from the top of the gradient, and 5 µl of each were electrophoresed in a 10% SDS-PAG. Full length CRD-BP and luciferase protein were quantified by PhosphorImager analysis using the ImageQuant program (Molecular Dynamics). Ribosomal RNA from each fraction was extracted, electrophoresed in a 1% agarose gel, and visualized by staining with ethidium bromide.

B. Results

Cloning the cDNA encoding the CRD-BP, a novel KH-domain RNA binding protein. Two preparations of highly purified CRD-BP were isolated from human K562 cell polysomes in separate experiments. Each preparation was microsequenced, and each gave a different, nonoverlapping sequence, which was P-A-Q-V-G-A-I-Q/I-G-k/r-I/K-Y/G-Q-X-i/l-k (SEQ ID NO:45) from the first and -N-E-L-Q-N-L-T-A-A-E-V-V-V-P (SEQ ID NO:46) from the second. Lower case letters indicate residues of less confidence than upper case letters. A K562 cDNA library was then screened by PCR using degenerate primers based on the amino and carboxy termini of the second peptide (Experimental Procedures). A 45 bp product was generated, subcloned, sequenced, and found to encode the second amino acid sequence. Subsequent PCR amplification and library screening identified a 1069 bp partial human cDNA containing an open reading frame (ORF) that included both peptide sequences obtained by microsequencing.

In order to continue our analysis of the properties and developmental regulation of the mouse CRD-BP, we then exploited the human cDNA sequence to isolate a putative mouse CRD-BP cDNA (Experimental Procedures). A clone containing at least a portion of the 5'-UTR, a complete coding region, and a complete 3'-UTR was obtained and sequenced (FIG.1). Two in-frame AUG start codons are present near the 5' terminus of the cDNA. We have tentatively designated the downstream AUG as the translation start site, because it is embedded within a sequence that is preferred as a translation start signal (36). In contrast, the upstream AUG is not within a preferred translation start motif.

The predicted sequence of the murine cDNA contains several KH domains and an RGG box, which are characteristic motifs found in some RNA-binding proteins. There are four KH domains arranged as two pairs of repeats (FIG. 1, double underlines). Each repeat pair is separated by approximately 30 residues, and the two pairs of repeats are separated by 78 residues. The putative RGG box (boxed) is located upstream of the KH domains. There are two putative nuclear export signals (overlined). One is similar to that found in the FMR RNA-binding protein (FMRP), which is associated with familial mental retardation (37–39). The other is similar to that in the HIV Rev protein. There is also a putative nuclear localization signal (underlined).

Figure 2C-2:
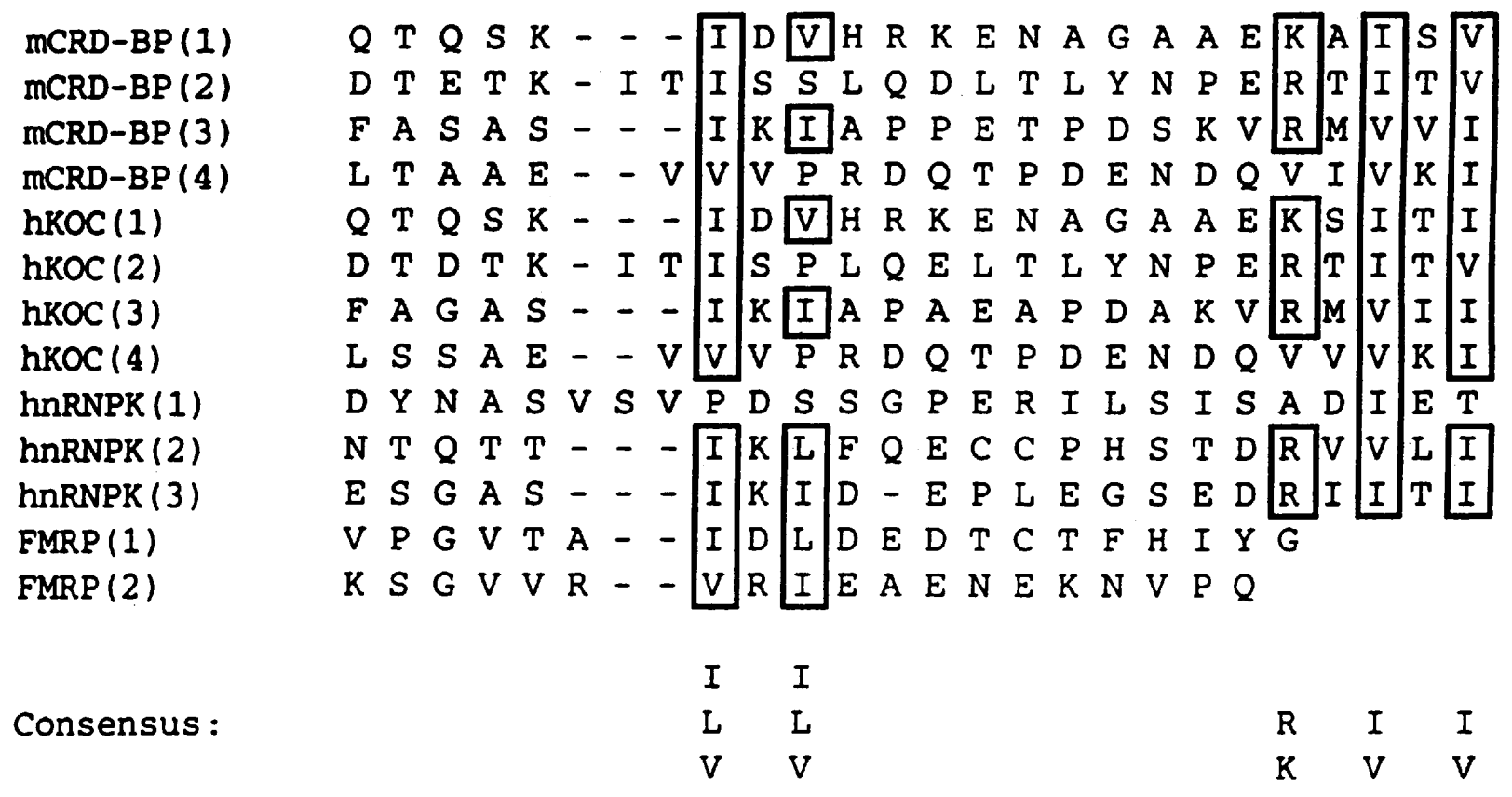

The RGG, nuclear export, and KH domain regions of the CRD-BP are similar to those found in several other RNA-binding proteins (FIG. 2). Moreover, the human and murine CRD-BP sequences are similar to a human cDNA called hKOC, an acronym for human KH domain protein overexpressed in human cancer (FIG. 2). The hKOC open reading frame encodes a protein of unknown function that was cloned on the basis of its overexpression in human pancreatic cancer tissue (40). The mouse CRD-BP coding region is 88.8% and 99.1% identical to the coding region of the human CRD-BP at the nucleic acid and protein sequence levels, respectively. For comparison, mouse CRD-BP is 66.6% and 74.0% identical to the hKOC coding region at the nucleic acid and protein levels, respectively. Based on these comparisons and on the data presented below, we conclude that our cDNA encodes CRD-BP and is not the mouse homologue of human KOC. Additional evidence (presented below) suggests that the CRD-BP and hKOC are members of a new subfamily of KH domain containing RNA-binding proteins.

Comparison of in vitro synthesized CRD-BP with cell-derived CRD BP. To determine whether our murine cDNA clone encoded full-length CRD-BP with the expected properties of a c-myc mRNA-binding protein, we synthesized the protein in vitro and analyzed it by immunoblotting and gel retardation assays. Reticulocyte transcription/translation reactions were programmed with CRD-BP cDNA subcloned into a pSPUTK vector. The CRD-BP sequences in the subclone began with the AUG denoted as the translation start site in FIG. 1. This subclone did not contain the upstream, in-frame AUG. The translation extract was fractionated by SDS-PAGE and analyzed by immunoblotting with anti-CRD-BP antibody. A protein of ~68 kDa from the cDNA translation was recognized by anti-CRD-BP antibody and migrated close to the positions of authentic CRD-BP from human (K562) and mouse (NIH/3T3) cells (FIG. 3, lanes 1–3). An immunoreactive band was not observed in control lanes containing extract programmed with the pSPUTK vector (FIG. 3, lane 4) or with luciferase cDNA (data not shown), indicating that the antibody specifically detected CRD-BP and not an endogenous reticulocyte protein. Therefore, our cDNA encodes CRD-BP. The cross-reacting band (p85) seen in the K562 and NIH/3T3 RSW lanes is a protein observed previously (32). Its identity and function are unknown. p85 does not bind c-myc CRD RNA (32), and it localizes to different subcellular fractions when compared to CRD-BP (see below).

Figure 4A:
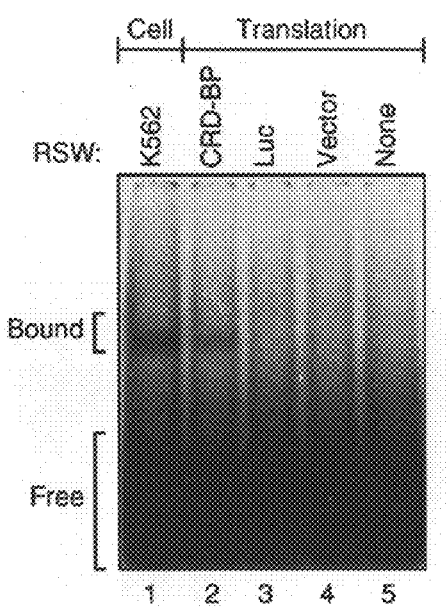
FIG. 4. Gel retardation assay showing specific binding of recombinant CRD BP to c-myc CRD RNA. (A) RSW was prepared from K562 cell polysomes and from transcription/translation reactions programmed with CRD-BP cDNA, luciferase cDNA (Luc), or vector DNA. Equivalent volumes (2 $\mu$l) of each RSW were incubated with 50,000 cpm of synthetic c-myc CRD $^{32}$P-RNA. RNA/protein complexes were separated from free (unbound) probe by electrophoresis in a 6% nondenaturing PAG. "None" indicates a gel retardation reaction to which no protein was added. The positions of CRD-BP/CRD complexes (Bound) and of unbound (Free) RNA are indicated on the left. (B) Competition assay. The indicated RSW was incubated with c-myc CRD $^{32}$P-RNA in the presence or absence of buffer (None) or a 200-fold molar excess of unlabeled synthetic c-myc CRD RNA or β-Globin RNA. RNA/protein complexes were then separated in a 6% nondenaturing PAG. The positions of CRD-BP/CRD complexes (Bound) and of unbound (Free) RNA are indicated on the left.

Gel retardation assays were performed to determine if recombinant CRD-BP could bind specifically to c-myc CRD RNA. In preliminary experiments, we noted that most of the recombinant CRD-BP co-fractionated with reticulocyte ribosomes (see below). Therefore, the gel retardation assays were performed using RSW from cells or from reticulocyte translation reactions. RSW's were incubated with c-myc CRD $^{32}$P-RNA, and RNA/protein complexes were resolved from free $^{32}$P-RNA by non-denaturing gel electrophoresis. An RNA/protein complex was observed with protein from K562 cells and from the translation extract programmed with CRD-BP cDNA (FIG. 4A, lanes 1 and 2, respectively). These complexes migrated to similar or identical positions in the gel.

An RNA/protein complex was not observed with protein from the luciferase (Luc), Vector, or no mRNA (None) control reactions (FIG. 4A, lanes 3–5). Therefore, in vitro synthesized CRD-BP, like its cell-derived counterpart, associates with c-myc CRD RNA in vitro.

Figure 4B:
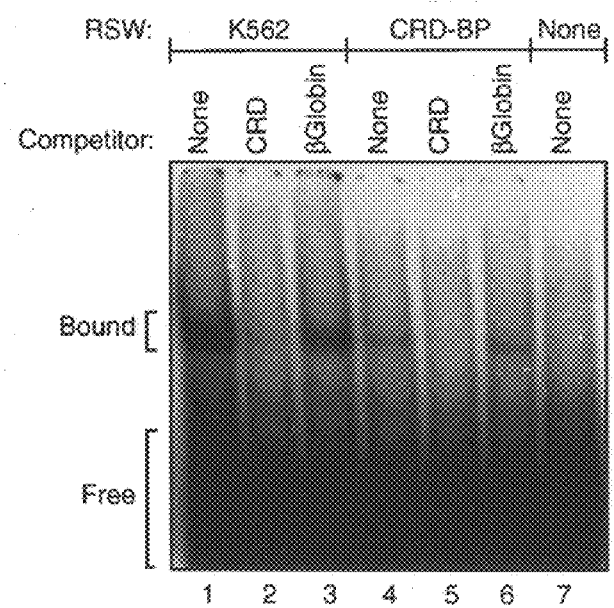

Previous work had shown that cell-derived CRD-BP did not bind to other RNAs we tested, suggesting that it had considerable specificity for c-myc CRD RNA (30, 31). A competition assay was performed to determine if recombinant CRD-BP exhibited similar specificity. RNA-protein binding reactions contained c-myc CRD $^{32}$P-RNA as probe plus RSW as a protein source. Reactions were supplemented with no competitor RNA or with a 200-fold molar excess of either unlabeled c-myc CRD RNA or β-globin RNA. The CRD BP/CRD $^{32}$P-RNA complex was competed by excess unlabeled CRD RNA but not by β-globin RNA (FIG. 4B). This result further confirms that this cDNA encodes functional c-myc CRD-BP.

Co-fractionation of recombinant CRD-BP with ribosomes in reticulocyte extracts. As noted above, preliminary experiments had indicated that a large percentage of recombinant CRD-BP co-sedimented with reticulocyte polysomes. It was important to confirm this finding, because reticulocytes contain no c-myc mRNA as measured by Northern blotting. Therefore, it was possible that the CRD-BP, like the FMRP (33), has an affinity for ribosomes even in the absence of what we believe to be its natural mRNA ligand. 35S-Labeled CRD-BP and luciferase were synthesized in reticulocyte extracts, and each extract was sedimented in a sucrose gradient. Fractions were collected and assayed for ribosome content by gel electrophoresis and for protein by gel electrophoresis and PhosphorImager analysis. Whereas all of the luciferase sedimented near the top of the gradient (FIG. 5, unfilled circles), greater than 95% of the CRD-BP co sedimented with monosomes and ribosomal subunits (filled circles). Therefore, the CRD BP can bind in vitro to ribosomes and ribosomal subunits in the absence of c-myc mRNA.

Figure 5:
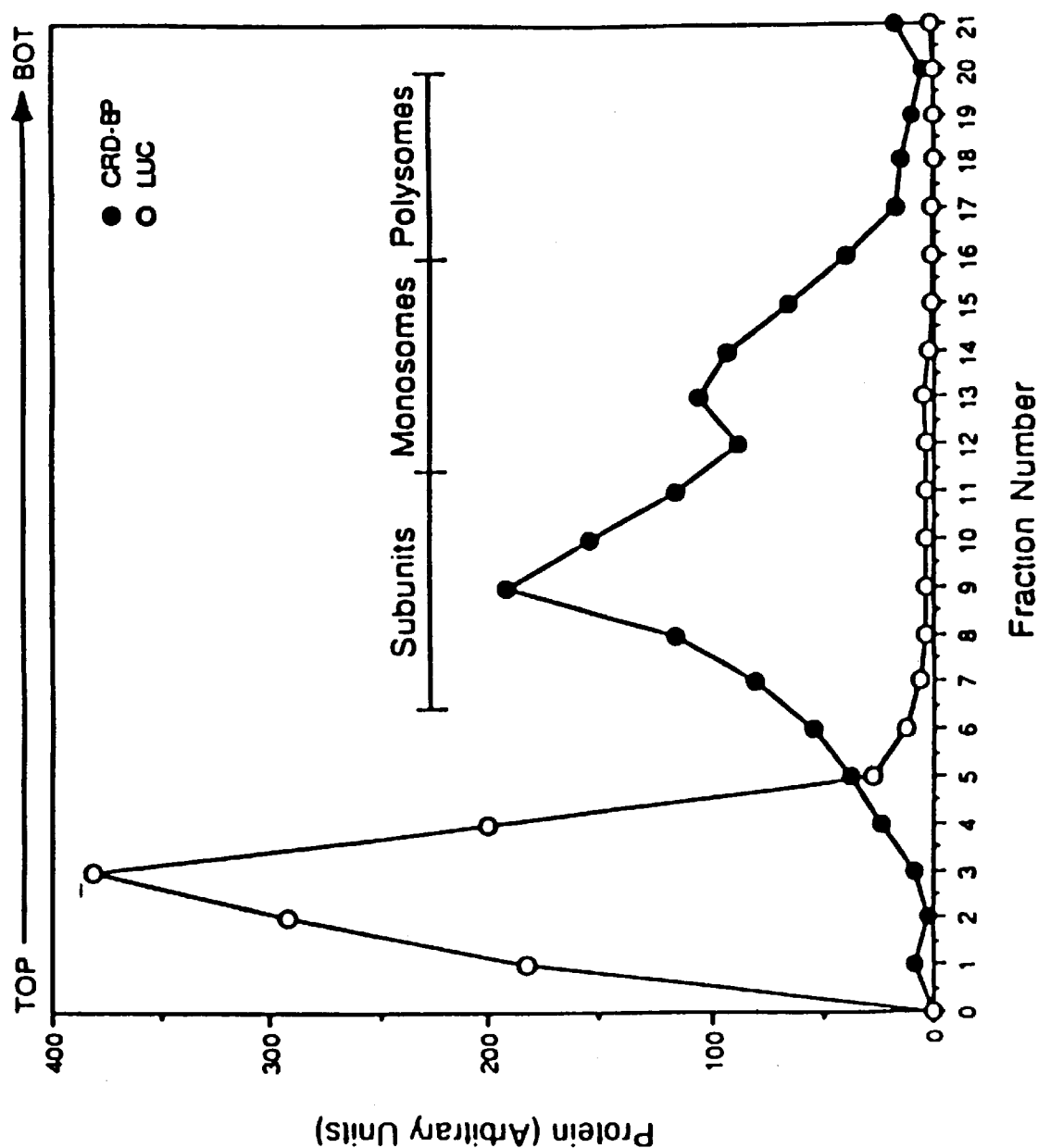
FIG. 5. Co-fractionation of recombinant CRD-BP with reticulocyte ribosomes and ribosomal subunits. Radiolabeled recombinant CRD-BP (filled circles) and luciferase (LUC; unfilled circles) were synthesized in separate reticulocyte translation assays. Each extract was then fractionated by sedimentation through a 20–40% linear sucrose gradient. Equivalent amounts of each gradient fraction were analyzed for radiolabeled protein by electrophoresis in a 10% SDS-PAG and quantitation in the Phosphorimager. The quantity of CRD-BP and luciferase is given in arbitrary units. The locations of ribosomal subunits, monosomes, and polyribosomes were determined by measuring A260 and by electrophoresing a portion of each fraction in an agarose gel, to identify 18S and 28S rRNAs.

Localization of CRD-BP to the cytoplasm and co-fractionation with ribosomes and ribosomal subunits. The CRD-BP is located primarily in the cytoplasmic fraction of K562 cell extracts, and much of it is associated with polysomes (ref. 31 and data not shown). This observation is consistent with its putative role as an mRNA-binding protein. However, the amount of CRD-BP per K562 cell exceeds the amount of c-myc mRNA by at least 1000-fold (31). Several factors could account for the "excess" CRD-HP in these cells: i) The CRD-BP might be associated with other mRNAs besides c-myc. ii) A portion of it might associate with ribosomes and/or ribosomal subunits, as is the case with FMRP (33). An association between the CRD-BP and ribosomes in cells would be consistent with the association of newly synthesized CRD-BP with reticulocyte ribosomes (FIG. 5). Experiments are in progress to determine whether the CRD-BP is bound to c-myc mRNA in cells. To determine how much of it co-fractionates with cell ribosomes and ribosomal subunits and how much, if any, co-fractionates with nuclei, exponentially growing K562 cells were harvested, lysed, and separated into 6 fractions (Experimental Procedures). Equal cell equivalents of each fraction were analyzed by immunoblotting with an anti-CRD-BP antibody. At least 95% of the total cell CRD-BP was in the polysome fraction, and greater than 90% of this CRD-BP was eluted in the one molar salt wash (FIG. 6A, RSW). Little or no CRD-BP was detected in fractions containing nuclei or post-polysomal supernatant (FIG. 6A, Nuclei and S130, respectively). The absence of CRD-BP in these fractions could not be explained by indiscriminate proteolysis during sample preparation, because HSP-90 was detected in all of the fractions (FIG. 6B). Some p85 was detected in both the nuclear and polysomal fractions. This result, coupled with those presented below, further confirms that the CRD-BP and the cross-reacting p85 do not co-localize in cells and are functionally distinct proteins.

To determine if at least some CRD-BP is associated with ribosomal subunits, K562 cell polysomes were purified by centrifugation and then resuspended in a buffer containing 20 mM EDTA, which dissociates polysomes into ribosomal subunits and free MRNP. The EDTA-treated polysomes were then fractionated in a sucrose gradient. Each gradient fraction plus material in the pellet at the bottom of the tube were analyzed for ribosomal RNA content by gel electrophoresis and for CRD-BP by immunoblotting. The small ribosomal subunits sedimented primarily in fractions 6–11, while the large subunits were in fractions 10–14 (FIG. 7, panels A and B). The CRD-BP co-sedimented with the subunits and was also detected in the pelleted material, which is expected to contain undissociated polysomes and monosomes (FIG. 7C). Therefore, the CRD-BP co-fractionates with ribosomal subunits in K562 cells. The nature of the CRD-BP/subunit association is unclear. In view of the broad fractionation range of the CRD-BP, we have not attempted to quantitate relative CRD-BP levels from one fraction to the next.

Data from gel retardation and RNA-protein binding experiments indicate that p85 does not bind to the c-myc CRD RNA (31, 32). FIG. 7C also shows that the small portion of p85 that does co-pellet with polysomes is not bound to the dissociated ribosomal subunits. Rather, it sediments at the top of the gradient (FIG. 7C). Similar results were obtained using crude cytoplasmic lysate (S20) treated with EDTA (data not shown). In summary, p85 reacts with polyclonal anti-CRD-BP antibody but does not bind to c-myc CRD RNA (30, 31) and does not co-fractionate with the CRD-BP in cell lysates.

Figure 8A:
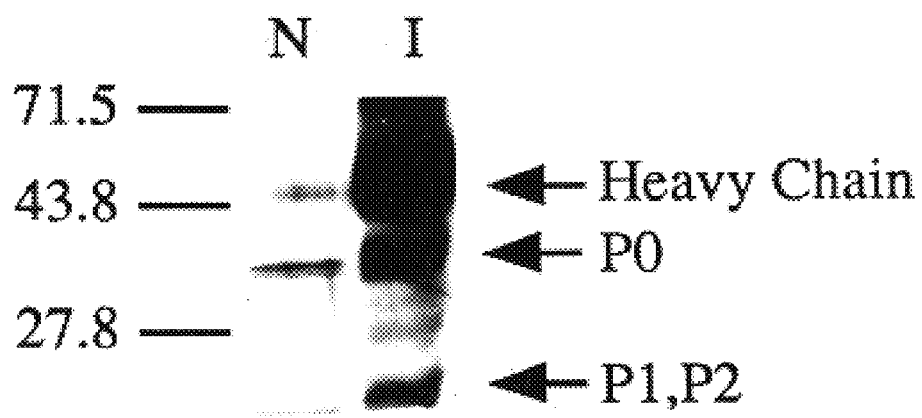
FIG. 8. Co-fractionation of the CRD-BP with 60S ribosomal subunits as determined by immunoprecipitation with anti P-protein antibody. An aliquot of EDTA dissociated K562 cell polysomes was incubated with anti-P protein antibody (I) or with normal human serum (N). Antibody-antigen complexes were immunoprecipitated (IP'd), and IP'd proteins were immunoblotted and analyzed using anti-P protein IgG (panel A) or anti-CRD-BP IgY (panel B). Immunoreactive proteins were visualized using ECL reagents. The locations of the P proteins ($P_0$, $P_1$ and $P_2$) and the CRD-BP are indicated on the right. The positions of prestained molecular mass markers are indicated in kDa on the left. Heavy chain indicates cross-reactivity with the IgG heavy chain on the membrane.
Figure 8B:
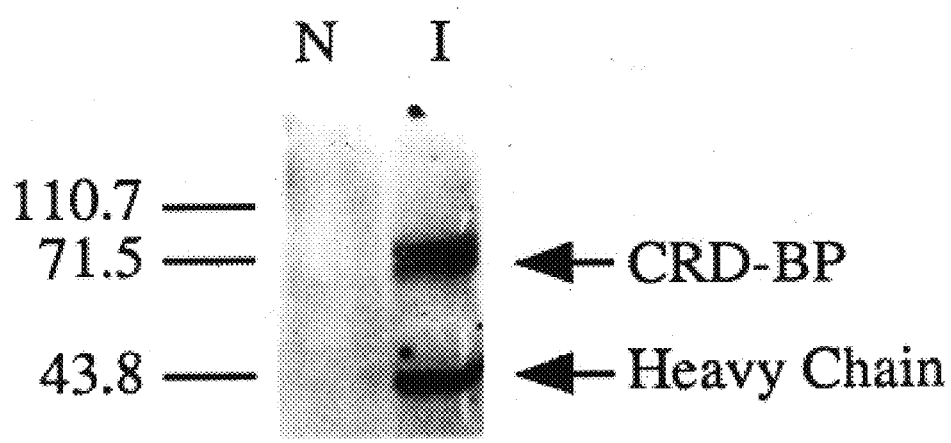

To verify the association of the CRD-BP with ribosomal subunits using an independent method, immunoprecipitation (IP) experiments were performed using P protein antibodies, which react specifically with proteins associated with the large (60S) subunit. K562 cell polysomes were dissociated into subunits in the presence of 20 mM EDTA and IP'd with anti-P antibody serum or normal human serum. The IP'd proteins were then analyzed by immunoblotting using antibodies against the P-proteins and the CRD-BP. The anti-P protein antibodies IP'd the three 60S proteins ($P_0$, $P_1$, and P₂), as expected (FIG. 8A, lane I). None of these proteins were IP'd by normal human serum (lane N). The anti-P protein antibodies also IP'd the CRD-BP (FIG. 8B, lane I). These findings confirm that the CRD-BP is associated with ribosomal subunits in K562 cell extracts.

C. Discussion

The CRD-BP is thought to stabilize c-myc mRNA by shielding its coding region from endonucleolytic attack is (22, 30, 31). In this respect, it might be similar to the iron response protein that binds to and protects the 3'-UTR of transferrin receptor mRNA (reviewed in 41). However, the CRD-BP differs from the iron response protein and from many other mRNA-binding proteins in at least two ways. (i) Most such proteins bind within the 3'-UTR, while the CRD-BP binds to the c-myc mRNA coding region. It does not bind in vitro to RNA substrates from either of the c-myc untranslated regions (30). The coding region of c-fos mRNA also contains an mRNA half-life determinant that is a protein-binding site (42). Perhaps the function of the myc and fos mRNA coding region determinants and their respective binding proteins is related to the regulation of myc and fos protein expression. (ii) The c-myc CRD-BP is developmentally regulated, being expressed abundantly in fetal and neonatal life but not in adult animals (32). Perhaps the CRD-BP has a special role in embryonic/fetal development.

The CRD-BP contains four KH domains and an RGG box, and it co-fractionates with polysomes and ribosomal subunits. These findings are consistent with it being an RNA-binding protein whose function is related in some way to translation and/or mRNA metabolism. The CRD-BP also co-fractionates with ribosomes in the absence of c-myc mRNA (FIG. 5). Perhaps it is bound both to c-myc mRNA and to ribosomes in intact cells. If so, it might be carried along with the translating ribosomes as a reservoir to be used when needed to bind to any contains a putative nuclear localization sequence and two putative nuclear export sequences (FIGS. 1 and 2). We do not know if the CRD-BP shuttles between the nucleus and the cytoplasm. If it does shuttle, however, it appears to spend most of its time in the cytoplasm of growing cells, because little of it is detected in the nucleus at steady-state (FIG. 6).

Consistent with the unique features of the CRD-BP noted above, the CRD-BP and hKOC protein appear to represent a unique subfamily of KH domain-containing RNA binding proteins. Other putative RNA-binding proteins, including the FUSE-binding protein, P-element somatic inhibitor, and C. elegans M88.5, resemble the CRD-BP in containing four KH domains (43). However, several structural features of these proteins distinguish them from CRD-BP and hKOC. The KH domains of the P-element somatic inhibitor and FUSE-binding proteins are located toward their amino termini and are organized as an evenly-spaced, four unit repeat. These proteins also contain either glycine rich or glutamine-rich stretches in their amino and carboxy termini. The overall organization of the four KH domains of M88.5 is most similar to CRD-BP and hKOC. It contains two pairs of KH domains separated by 83 amino acids. However, in contrast to CRD-BP and hKOC, the amino terminus of M88.5 is glutamine-rich and lacks an RGG box. The FUSE-binding protein contains a sequence resembling an RGG box, but this sequence is located between the third and fourth KH domains, which is not the case for the CRD-BP and hKOC protein. Finally, the core sequences of the KH domains of these other proteins are very different from those in either CRD-BP or hKOC.

Several structural and functional similarities are also noted between the CRD-BP and the FMRP, the protein encoded by the FMR1 gene, mutations in which are responsible for the most common form of inherited mental retardation (44, 45). Both proteins contain KH domains and an RGG box (37, 38) as well as nuclear import and export signals (39). Both proteins associate with ribosomes and probably with mRNA as well (33, 49, 46). Neither protein is required for cell viability, because individuals who fail to express FMRP survive, while perfectly normal adult animals do not express the CRD-BP at levels detectable by immunoblotting and/or gel retardation assays (32). There are also some significant differences between FMRP and CRD-BP, particularly in their expression patterns. Both are expressed abundantly during fetal life, but only FMRP is detected in adult tissues (47–49).

The structural features of the CRD-BP and its developmental regulation pattern suggest that it might be an oncofetal protein, for the following reasons: (i) It is expressed abundantly only in fetal and neonatal life (32). (ii) All of the mouse CRD-BP EST's that are currently in the database are derived from either fetal tissue or from cell lines, including embryonic stem cells. These include AA073173 (from 13 day old embryonic heart tissue), AA619650 and AA399833 (from a pre-implantation blastocyst), AA073514 (from the P19 embryonic carcinoma cell line treated with retinoic acid), and D76662 and D76781 (from the F9 embryonic carcinoma cell line). (iii) The CRD-BP is expressed in many cell lines, all of which are neoplastic or pre-neoplastic. It is expressed at high levels in K562, HeLa, and 3T3 cells (FIGS. 3 and 4 and data not shown) and at low levels in other lines such as HL60, a human promyelocytic leukemia cell, and H4IIE, a rat hepatoma cell (data not shown). (iv) It is similar but not identical to the hKOC protein that is over-expressed in pancreatic cancer and in some other tumors (FIG. 2 and ref. 40). If the CRD-BP is an oncofetal protein, it would join a growing list of RNA-binding proteins that influence the early development of the organism and/or that affect carcinogenesis. For example, mutations in the Elav proteins influence Drosophila development (reviewed in 50–53), while mutations in other RNA-binding protein genes result in male infertility or mental retardation (44).

D. Detecting the CRD-BP in Clinical Samples

Human tumor tissues were provided by physicians and surgeons at the UW-Madison Clinical Cancer Center. The tissues were homogenized, and a crude cytoplasmic extract was prepared. The extract was then fractionated by two-dimensional gel electrophoresis at Kendrick Laboratories (Madison, Wis.). Following electrophoresis in the second dimension, the proteins were transferred to PVDF membranes and returned to our laboratory.

CRD-BP was visualized by incubating the membranes with antibodies to mouse CRD-BP. These antibodies cross-react with human CRD-BP.

Findings are as follows:

1. We detect abundant CRD-BP in human breast cancer, colon cancer, and pancreatic cancer tissues. We expect to find similar results with other non-hemopoietic cancers.

2. A significantly smaller amount of CRD-BP is detected in one normal human breast tissue sample.

3. No CRD-BP is detected in several human leukemia samples.

Our conclusion from these studies is that the CRD-EP is overexpressed in non-leukemia human carcinomas.

REFERENCES

1. Ayer, D. E. and Eisenman, R. N., *Genes Devel.* 7:2110–2119, 1993.

2. Ayer, D. E., Kretzner, L., and Eisenman, R. N., *Cell* 72:211–222, 1993.
3. Zervos, A. S., Gyuris, J., and Brent, R., *Cell* 72:223–232, 1993.
4. Spencer, C. A. and Groudine, M., *Adv. Canc. Res.* 56:1–48, 1991.
5. Coppola, J. A. and Cole, M. D., *Nature* 320:760–763, 1986.
6. Freytag, S. O., Dang, C. V., and Lee, W. M. F., *Cell Growth Diff.* 1:339–343, 1990.
7. Evan, G. I., Wyllie, A. H., Gilbert, C. S., Littlewood, T. D., Land, H., Brooks, M., Waters, C. M., Penn, L. Z., and Hancock, D. C., *Cell* 69:119–128, 1992.
8. Adams, J. M., Harris, A. W., Pinkert, C. A., Corcoran, L. M., Alexander, W. S., Cory, S., Palmiter, R. D., and Brinster, R. L., *Nature* 318:533–538, 1985.
9. Klein, G., *Genes, Chromosomes, Cancer* 1:3–8, 1989.
10. Lüscher, B. and Eisenman, R. N., *Genes Devel.* 4:2025–2035, 1990.
11. Spotts, G. D. and Hann, S. R., *Mol. Cell. Biol.* 10:3952–3964, 1990.
12. Lutterbach, B. and Hann, S. R., *Molec. Cell. Biol.* 14:5510–5522, 1994.
13. Morello, D., Asselin, C., Lavenu, A., Marcu, K. B., and Babinet, C. *Oncogene* 4:955–961, 1989.
14. Gruppuso, P. A., FitzGerald, M. J., and Fausto, N., *Pediatr. Res.* 33:49A, 1993.
15. Morello, D., Lavenu, A., and Babinet, C., *Oncogene* 5:1511–1519, 1990.
16. Steer, C. J., *FASEB J.* 10:559–573, 1996.
17. Jones, T. R. and Cole, M. D., *Mol. Cell. Biol.* 7:4513–4521, 1987.
18. Wisdom, R. and Lee, W., *J. Biol. Chem.* 265:19015–19021, 1990.
19. Wisdom, R. and Lee, W., *Genes and Devel.* 5:232–243, 1991.
20. Yeilding, N. M., Rehman, M. T., and Lee, W. M. F., *Mol. Cell. Biol.* 16:3511–3522, 1996.
21. Yeilding, N. M. and Lee, W. F., *Mol. Cell. Biol.* 17:2698–2707, 1997.
22. Herrick, D. J. and Ross, J., *Mol. Cell. Biol.* 14:2119–2128, 1994.
23. Lavenu, A., Pistoi, S., Pournin, S., Babinet, C., and Morello, D., *Mol. Cell. Biol.* 15:4410–4419, 1995.
24. Morello, D., Lavenu, A., Pournin S., and Babinet, C., *Oncogene* 8:1921–1929, 1993.
25. Pistoi, S., Roland, J., Babinet, C., and Morello, D., *Molec. Cell. Biol.* 16:5107–5116, 1996.
26. Ross, J. and Kobs, G., *J. Mol. Biol.* 188:579–593, 1986.
27. Ross, J., Peltz, S. W., Kobs, G., and Brewer, G., *Molec. Cell. Biol.* 6:4362–4371, 1986.
28. Peltz, S. W. and Ross, J., *Molec. Cell. Biol.* 7:4345–4356, 1987.
29. Brewer, G. and Ross, J., *Mol. Cell. Biol.* 8:1697–1708, 1988.
30. Bernstein, P. L., Herrick, D. J., Prokipcak, R. D., and Ross, J., *Genes Devel.* 6:642–654, 1992.
31. Prokipcak, R. D., Herrick, D. J., and Ross, J., *J. Biol. Chem.* 269:9261–9269, 1994.
32. Leeds, P., Kren, B. T., Boylan, J. M., Betz, N. A., Steer, C. J., Gruppuso, P. A., and Ross, J., *Oncogene* 14:1279–1286, 1997.
33. Siomi, M. C., Zhang, Y., Siomi, H., and Dreyfuss, G., *Mol. Cell. Biol.* 16:3825–3832, 1996.
34. Elkon, K., Skelly, S., Parnassa, A., Moller, W., Dahno, W., Weissbach, H., and Brot, N., *Proc. Natl. Acad. Sci. USA* 83:7419–7423, 1986.
35. Henshaw, E. C., *Methods in Enzymology* 59:410–421, 1979.
36. Kozak, M., *J. Cell Biol.* 108:229–241, 1989.
37. Ashley, C. T., Wilkinson, K. D., Reines, D., and Warren, S. T., *Science* 262:563–565, 1993.
38. Siomi, H., Siomi, M. C., Nussbaum, R. L., and Dreyfuss, G., *Cell* 74:291–298, 1993.
39. Eberhart, D. E., Malter, H. E., Feng, Y., and Warren, S. T., *Hum. Molec. Gen.* 5:1083–1091, 1996.
40. Müeller-Pillasch, F., Lacher, U., Wallrapp, C., Micha, A., Zimmerhackl, F., Hameister, H., Varga, G., Friess, H., Büchler, M., Beger, H. G., Vila, M. R., Adler, G., and Gress, T. M., *Oncogene* 14:2729–2733, 1997.
41. Harford, J. B., Rouault, T. A., and Klausner, R. D., Iron Metabolism in Health and Disease. J. H. Brock, J. W. Halliday, M. J. Pippard, and L. W. Powell (eds.), W. B. Saunders, Philadelphia, pp. 123–149, 1994.
42. Chen, C-Y., You, Y., and Shyu, A-B., *Mol. Cell. Biol.* 12:5748–5757, 1992.
43. Musco, G., Stier, G., Joseph, H., Antonietta, M., Morelli, C., Nilges, M., Gibson, T. J., Pastore, A., *Cell* 85:237–245, 1996.
44. Cooke, H. J. and Elliott, D. J., *Trends Genet.* 13:87–89, 1997.
45. Nussbaum, N. L. and Ledbetter, D. H., Metabolic Basis of Inherited Disease, C. R. Scriver, A. Beaudet, W. S. Sly, and D. Valle, eds. (McGraw-Hill, N. Y.), pp. 759–810, 1995.
46. Khandjian, E. W., Corbin, F., Woerly, S., and Rousseau, F., *Nature Genetics* 12:91–93, 1996.
47. Feng, Y., Gutekunst, C. A., Eberhart, D. E., Yi, H., Warren, S. T., and Hersch S. M., *J. Neurosci.* 17:1539–1547, 1997.
48. Khandjian, E. W., Fortin, A., Thibodeau, A., Tremblay, S., Cote, F., Devys, D., Mandel, J. L., and Rousseau, F., *Hum. Molec. Gen.* 4:783–789, 1995.
49. Hinds, H. L., Ashley, C. T., Sutcliff, J. S., Nelson, D. L., Warren, S. T., Housman, D. E., and Schalling, M., *Nature Genetics* 3:36–43, 1993.
50. Burd, C. G. and Dreyfuss, G., *Science* 265:615–621, 1994.
51. Herschlag, D., *J. Biol. Chem.* 270:20871–20874, 1995.
52. Shamoo, Y., Abdul-Manan, N., and Williams, K. R., *Nucl. Acids Res.* 23, 725–728, 1995.
53. Gao, F-B. and Keene, J. D., *J. Cell Science* 109:579–589, 1996.

I claim:

1. A method of diagnosing the presence or absence of breast cancer in a human patient comprising the steps of:

a) examining patient breast tissue for CRD-BP expression level; and b) comparing the result of step (a) with the expression level in non-cancerous tissue of the same tissue type, wherein an increased CRD-BP level in the patient tissue compared to the non-cancerous tissue is diagnostic of cancer.

* * * * *